United States Patent
Fontanazzi et al.

(10) Patent No.: US 10,265,459 B2
(45) Date of Patent: *Apr. 23, 2019

(54) APPARATUS FOR DETERMINING A PARAMETER INDICATIVE OF THE PROGRESS OF AN EXTRACORPOREAL BLOOD TREATMENT

(71) Applicant: Gambro Lundia AB, Lund (SE)

(72) Inventors: Francesco Fontanazzi, Modena (IT); Alessandro Surace, Carpi (IT); Francesco Rosati, Fano (IT)

(73) Assignee: GAMBRO LUNDIA AB, Lund (SE)

( * ) Notice: Subject to any disclaimer, the term of this patent is extended or adjusted under 35 U.S.C. 154(b) by 0 days.

This patent is subject to a terminal disclaimer.

(21) Appl. No.: 15/911,448

(22) Filed: Mar. 5, 2018

(65) Prior Publication Data
US 2018/0193547 A1 Jul. 12, 2018

Related U.S. Application Data

(63) Continuation of application No. 14/441,897, filed as application No. PCT/IB2013/059711 on Oct. 28, 2013, now Pat. No. 9,943,636.

(60) Provisional application No. 61/726,231, filed on Nov. 14, 2012.

(30) Foreign Application Priority Data

Nov. 14, 2012 (EP) ..................... 12007705

(51) Int. Cl.
*A61M 1/00* (2006.01)
*A61M 1/36* (2006.01)
(Continued)

(52) U.S. Cl.
CPC .............. *A61M 1/367* (2013.01); *A61M 1/16* (2013.01); *A61M 1/1607* (2014.02);
(Continued)

(58) Field of Classification Search
CPC .. A61M 1/367; A61M 1/1607; A61M 1/1609; A61M 1/1613; A61M 1/1617;
(Continued)

(56) References Cited

U.S. PATENT DOCUMENTS 5,024,756 A 6/1991 Sternby
5,100,544 A 3/1992 Polaschegg
(Continued)

FOREIGN PATENT DOCUMENTS

CA 2 336 923 1/2000
DE 196 46 775 5/1998
(Continued)

OTHER PUBLICATIONS

International Search Report and Written Opinion dated Oct. 16, 2013, for related International Appln. No. PCT/IB2013/054875.
(Continued)

*Primary Examiner* — Philip R Wiest
(74) *Attorney, Agent, or Firm* — K&L Gates LLP

(57) ABSTRACT

An apparatus for extracorporeal treatment of blood (1) comprising a treatment unit, a blood withdrawal line, a blood return line, a preparation line and a spent dialysate line. A control unit (10) is configured to calculate values of a parameter relating to treatment effectiveness based on measures of the conductivity in the spent dialysate line. The value of the effectiveness parameter is calculated using one or more values representative of the conductivity in the spent dialysate line obtained relying on a mathematical model.

24 Claims, 9 Drawing Sheets

(51) Int. Cl.
*A61M 1/16* (2006.01)
*G05B 13/04* (2006.01)
*G05D 7/06* (2006.01)
*G06F 17/10* (2006.01)

(52) U.S. Cl.
CPC ........ *A61M 1/1609* (2014.02); *A61M 1/1613* (2014.02); *A61M 1/1617* (2014.02); *G05B 13/04* (2013.01); *G05D 7/0617* (2013.01); *G06F 17/10* (2013.01); *A61M 2205/3317* (2013.01); *A61M 2205/3324* (2013.01); *A61M 2205/3334* (2013.01); *A61M 2205/3393* (2013.01); *A61M 2209/02* (2013.01)

(58) Field of Classification Search
CPC ............ A61M 1/16; A61M 2205/3319; A61M 2205/3324; A61M 2205/3334; A61M 2205/3393; G05B 13/04
See application file for complete search history.

(56) References Cited

U.S. PATENT DOCUMENTS

| | | | |
|---|---|---|---|
| 5,567,320 A | | 10/1996 | Goux et al. |
| 6,110,384 A | * | 8/2000 | Goux .................... A61M 1/16 210/645 |
| 6,187,199 B1 | | 2/2001 | Rainer |
| 6,602,424 B1 | | 8/2003 | Kramer et al. |
| 2007/0131595 A1 | | 7/2007 | Jansson et al. |
| 2010/0004523 A1 | | 1/2010 | August et al. |

FOREIGN PATENT DOCUMENTS

| | | |
|---|---|---|
| EP | 0 920 877 | 6/1999 |
| EP | 2380609 | 10/2011 |
| FR | 2 713 936 | 6/1995 |
| WO | 00 02604 | 1/2000 |
| WO | 2012127298 | 9/2012 |

OTHER PUBLICATIONS

Gotch et al., "A mechanistic analysis of the National Cooperative Dialysis Study (NCDS)", Kidney International, 1985, vol. 28, pp. 526-534.
European Office Action—Application No. 12198335.7 dated May 17, 2016.
International Search Report—PCT/IB2013/060984—Dated Jul. 7, 2014.
International Search Report—PCT/IB2013/059711—dated Apr. 14, 2014—7 pages.
Written Opinion—PCT/IB2013/059711—dated Apr. 14, 2014—8 pages.

* cited by examiner

APPARATUS FOR DETERMINING A PARAMETER INDICATIVE OF THE PROGRESS OF AN EXTRACORPOREAL BLOOD TREATMENT

PRIORITY CLAIM

The present application is a continuation of U.S. application Ser. No. 14/441,897, filed on May 11, 2015, entitled "Apparatus for Determining a Parameter Indicative of the Progress of an Extracorporeal Treatment", which is a National Phase of International Application No. PCT/IB2013/059711, filed on Oct. 28, 2013, which claims priority to European Patent Application No. 12007705.2, filed Nov. 14, 2012, and U.S. Provisional Application No. 61/726,231, filed Nov. 14, 2012, the entire contents of each of which are incorporated herein by reference and relied upon.

BACKGROUND

The invention relates to an apparatus for determining a parameter indicative of the progress of an extracorporeal blood treatment (referred to as effectiveness parameter), in particular a purification treatment whose purpose is to alleviate renal insufficiency, such as—without limitation—hemodialysis or hemodiafiltration. It is also disclosed a method of determining said parameter indicative of the progress of an extracorporeal blood treatment. For instance, the parameter may be one of:
- the concentration in the blood of a given solute (for example, sodium),
- the actual dialysance D or the actual clearance K of the exchanger for a given solute (the dialysance D and the clearance K representing the purification efficiency of the hemodialyzer or hemofilter used in the blood treatment),
- the dialysis dose administered after a treatment time t, which, according to the work of Sargent and Gotch, may be linked to the dimensionless ratio Kt/V, where K is the actual clearance in the case of urea, t the elapsed treatment time and V the volume of distribution of urea, i.e. the total volume of water in the patient (Gotch F. A. and Sargent S. A., "A mechanistic analysis of the National Cooperative Dialysis Study (NCDS)", Kidney Int. 1985, Vol. 28, pp. 526-34). The dialysis dose—as above defined—is an integrated value $\int K(t)dt/V$ across a time interval, e.g. the dose after treatment time $t_n$ is the integral from the beginning of treatment until time instant $t_n$.

In an haemodialysis treatment a patient's blood and a treatment liquid approximately isotonic with blood flow are circulated in a respective compartment of haemodialyser, so that, impurities and undesired substances present in the blood (urea, creatinine, etc.) may migrate by diffusive transfer from the blood into the treatment liquid. The ion concentration of the treatment liquid is chosen so as to correct the ion concentration of the patient's blood.

In a treatment by haemodiafiltration, a convective transfer by ultrafiltration, resulting from a positive pressure difference created between the blood side and the treatment-liquid side of the membrane of an hemodiafilter, is added to the diffusive transfer obtained by dialysis.

It is of interest to be able to determine, throughout a treatment session, one or more parameters indicative of the progress of the treatment so as to be able, where appropriate, to modify the treatment conditions that were initially fixed or to at least inform the patient and the medical personnel about the effectiveness of the treatment.

The knowledge of one or more of the following parameters may make it possible to follow the progress of the treatment, and for instance may allow assessing the suitability of the initially fixed treatment conditions:
- the concentration in the blood of a given solute (for example, sodium),
- the actual dialysance D or the actual clearance K of the exchanger for solute (the dialysance D and the clearance K representing the purification efficiency of the exchanger),
- the dialysis dose administered after a treatment time Kt/V, where K is the actual clearance in the case of urea, t the elapsed treatment time and V the volume of distribution of urea.

The determination of these parameters requires precise knowledge of a physical or chemical characteristic of the blood. As it can be understood, determination of this characteristic cannot in practice be obtained by direct measurement on a specimen for therapeutic, prophylactic and financial reasons. Indeed, it is out of the question taking—in the course of a treatment—multiple specimens necessary to monitor the effectiveness of the treatment from a patient who is often anemic; furthermore, given the risks associated with handling specimens of blood which may possibly be contaminated, the general tendency is to avoid such handling operations; finally, laboratory analysis of a specimen of blood is both expensive and relatively lengthy, this being incompatible with the desired objective of knowing the effectiveness of a treatment while the treatment is still ongoing.

Several methods have been proposed for in vivo determining haemodialysis parameters without having to take measurements on blood samples.

Document EP 0547025 describes a method for determining the concentration of a substance, such as sodium, in a patient's blood subjected to a haemodialysis treatment. This method also makes it possible to determine the dialysance D—for example for sodium—of the haemodialyser used. The method comprises the steps of circulating a first and a second haemodialysis liquids having different sodium concentrations in succession through the haemodialyser, measuring the conductivity of the first and second dialysis liquids upstream and downstream of the haemodialyser, and computing the concentration of sodium in the patient's blood (or the dialysance D of the haemodialyser for sodium) from the values of the conductivity of the liquid which are measured in the first and second dialysis liquids upstream and downstream of the haemodialyser.

Document EP 0658352 describes another method for the in vivo determination of haemodialysis parameters, which comprises the steps of: making at least a first and a second treatment liquids, having a characteristic (the conductivity, for example) associated with at least one of the parameters (the ion concentration of the blood, the dialysance D, the clearance K, Kt/V, for example) indicative of the treatment, flow in succession through the haemodialyser, the value of the characteristic in the first liquid upstream of the exchanger being different from the value of the characteristic in the second liquid upstream of the hemodialyzer; measuring, in each of the first and second treatment liquids, two values of the characteristic, respectively upstream and downstream of the hemodialyzer; making a third treatment liquid flow through the hemodialyzer while the characteristic of the second liquid has not reached a stable value downstream of the hemodialyzer, the value of the characteristic in the third liquid upstream of the hemodialyzer being different from the value of the characteristic in the second liquid upstream of the hemodialyzer; measuring two values of the characteristic in the third liquid, respectively upstream and downstream of the hemodialyzer; and computing at least one value of at least one parameter indicative of the progress of the treatment from the measured values of the characteristic in the first, second and third treatment liquids.

Another method for the in vivo determination of the haemodialysis parameters which does not require taking measurements on blood samples is described in document EP 0920877. This method includes the steps of: making a treatment liquid flow through the exchanger, this treatment liquid having a characteristic which has an approximately constant nominal value upstream of the exchanger; varying the value of the characteristic upstream of the exchanger and then re-establishing the characteristic to its nominal value upstream of the exchanger; measuring and storing in memory a plurality of values adopted by the characteristic of the treatment liquid downstream of the exchanger in response to the variation in the value of this characteristic caused upstream of the exchanger; determining the area of a downstream perturbation region bounded by a baseline and a curve representative of the variation with respect to time of the characteristic; and computing the parameter indicative of the effectiveness of a treatment from the area of the downstream perturbation region and from the area of an upstream perturbation region bounded by a baseline and a curve representative of the variation with respect to time of the characteristic upstream of the exchanger.

With the aim of further improving the above methods, document US 2001004523 describes a solution for continuously determining a parameter (D, Cbin, K, Kt/V) indicative of the effectiveness of an extracorporeal blood treatment comprising the steps of: causing a succession of sinusoidal variations in the characteristic (Cd) a treatment liquid upstream of the exchanger, continuously storing in memory a plurality of values ($Cd_{in1}$ ... $Cd_{inj}$ ... $Cd_{inp}$) of the characteristic (Cd) upstream of the exchanger, measuring and continuously storing in memory a plurality of values ($Cd_{out1}$ ... $Cd_{outj}$ ... $Cd_{outp}$) adopted by the characteristic (Cd) downstream of the exchanger in response to the variations in the characteristic (Cd) which are caused upstream of the exchanger, computing—each time that a predetermined number of new values ($Cd_{outj}$) of the characteristic (Cd) downstream of the exchanger has been stored—a parameter (D, Cbin, K, Kt/V) indicative of the effectiveness of the extracorporeal blood treatment, from a first series of values ($Cd_{in}$) of the characteristic (Cd) upstream of the exchanger, from a second series of values ($Cd_{outj}$) of the characteristic (Cd) downstream of the exchanger.

Although the above methods have been implemented, they may have certain limitations.

The above described methods require a modification of the value of a characteristic of the dialysis liquid (the conductivity, for example) and then the re-establishment of this characteristic to its initial value, which is generally the prescribed value for the treatment. Since, deviations from the prescription are not desirable and since the above described methods require a duration of the introduced modification, it derives that the effectiveness parameter measure may be carried out only few times during a treatment.

Furthermore, the above methods require the control system of the blood treatment apparatus to prevent execution of tasks, other than the one for measuring the effectiveness parameter, which may affect the concerned characteristic (conductivity/concentration) of the dialysis fluid at least until the complete measurement of the values taken by the conductivity/concentration downstream the dialyzer has been made. For instance, the user will not be allowed to execute a change prescription task while the control system is executing the effectiveness parameter detection. Moreover, while the control system is executing the effectiveness parameter detection, the control system will not execute other tasks taking an active control on the conductivity/composition of the dialysis liquid (e.g. tasks acting on the sodium concentration of the dialysis liquid in response to detection of certain parameters such as blood concentration). In other words, during the entire process of changing the conductivity/concentration of the dialysis liquid upstream the dialyzer or hemofilter and measuring the corresponding downstream conductivity/concentration change, the control system of the dialysis machine does not allow execution of other tasks which could affect the dialysis liquid conductivity or composition, thereby limiting flexibility of operation of the dialysis machine.

Moreover, the methods described above are sensitive to artifacts that may be present in the conductivity measured downstream the dialyzer which may be caused by a number of factors (e.g. bubbles present in the dialysis circuit, activation/deactivation of certain actuators such as pumps, opening or closing of valves, etcetera).

Furthermore, the characteristic in the liquid downstream the dialyzer may be difficult to accurately be measured, due to a number of factors. Indeed, in case of a step shaped upstream perturbation it may be difficult to measure the asymptotic value of the response unless measurements for the downstream conductivity are taken for a relatively long time. On the other hand, in case of a sinusoidal upstream perturbation which never leads to any equilibrium state it may be difficult to properly interpret sensor detections.

Moreover, the hydraulic delay, the damping effect caused by the dialyzer or hemofilter, the effect of the blood conductivity/concentration on the value of the baseline conductivity downstream the dialyzer of hemofilter, and the noise introduced by the machine and its components may render further difficult interpretation of the signals detected by the sensors, particularly in presence of a continuously varying perturbation.

It is therefore an object of the present invention to provide an apparatus and a method configured reliably calculate an effectiveness parameter a plurality of times during treatment without substantially impairing on prescription delivered to the patient and minimally affecting the operation flexibility of the blood treatment apparatus.

Moreover, it is an auxiliary object providing a method and an apparatus which are not very sensitive to incidents or noise or accidental detection errors which may arise during the measurement.

Additionally, it is an object providing a method and an apparatus which may be implemented with no need of high computational power.

Another auxiliary object is an apparatus capable of operating in a safe manner.

A further auxiliary object is an apparatus capable of automatically calculate the effectiveness parameter and inform the operator accordingly.

SUMMARY

At least one of the above objects is substantially reached by an apparatus according to one or more of the appended claims.

Apparatus and methods according to aspects of the invention and capable of achieving one or more of the above objects are here below described.

A 1st aspect concerns an apparatus for extracorporeal treatment of blood comprising:

- a blood treatment unit (2) having a primary chamber (3) and a secondary chamber (4) separated by a semipermeable membrane (5);
- a preparation line (19) having one end connected to an inlet of a secondary chamber (4) of the treatment unit (2) and configured to convey fresh treatment liquid to the secondary chamber (4), the fresh treatment liquid presenting a characteristic ($Cd_{in}$) which is either the conductivity in the fresh treatment liquid or the concentration of at least one substance (for instance sodium or calcium or potassium) in the fresh treatment liquid;
- a spent dialysate line (13) having one end connected to an outlet of said secondary chamber (4) and configured to remove spent liquid from the secondary chamber (4), the spent liquid presenting a characteristic ($Cd_{out}$) which is either the conductivity in the fresh treatment liquid or the concentration of at least one substance (for instance sodium or calcium or potassium) in the fresh treatment liquid;
- a control unit (10) configured for commanding execution of a task for determination of a parameter indicative of the effectiveness of the extracorporeal blood treatment, said task comprising the following steps:
  - receiving at least one parametric mathematical model (the model may be pre-stored in memory connected with the control unit or it may be entered by user via a user interface ort it may be transmitted to the control unit from a remote station) which puts into relation the characteristic ($Cd_{in}$) in the fresh treatment liquid with the characteristic ($Cd_{out}$) in the spent liquid, said parametric mathematical model presenting a prefixed number of free parameters;
  - causing an upstream variation of the value of the characteristic ($Cd_{in}$) in the fresh treatment liquid with respect to said prescription baseline ($Cd_{set}$) thereby causing a corresponding and timely delayed downstream variation of the same characteristic ($Cd_{out}$) in the spent liquid flowing in the spent dialysate line (13);
  - measuring a plurality of values taken by a reference portion (200) of said downstream variation of the characteristic ($Cd_{out}$) in the spent liquid, said reference portion having duration shorter than the entire duration of the downstream variation;
  - estimating said free parameters of the at least one parametric mathematical model by means of said reference portion measured values and identifying one single characteristic mathematical model which puts into relation the characteristic ($Cd_{in}$) in the fresh treatment liquid with the characteristic ($Cd_{out}$) in the spent liquid;
  - computing at least one value of a parameter (D, $Cb_{in}$, K, K-t/V) indicative of the effectiveness of the extracorporeal blood treatment by using said characteristic mathematical model and one or more values taken by the characteristic ($Cd_{in}$) in the fresh treatment liquid.

In a 2nd aspect according to the 1st aspect, the task which the control unit is configured to execute includes also the steps of:

- receiving at least one prescription baseline ($Cd_{set}$) for the characteristic ($Cd_{in}$) in the fresh treatment liquid;
- causing fresh treatment liquid to flow in the preparation line (19) to the secondary chamber (4) with the characteristic being at said prescription baseline ($Cd_{set}$);
- causing spent liquid to flow out of the secondary chamber (4) into the spent dialysate line (13).

In a 3rd aspect according to any one of the preceding aspects the step of computing at least one value of a parameter (D, $Cb_{in}$, K, K-t/V) indicative of the effectiveness of the extracorporeal blood treatment comprises:

- computing one or more significant values of said downstream variation of the characteristic ($Cd_{out}$), said significant value or values of the downstream variation relating to a time subsequent to the duration of the reference portion (200) and being computed by using said characteristic mathematical model;
- computing at least one value of a parameter (D, $Cb_{in}$, K, K-t/V) indicative of the effectiveness of the extracorporeal blood treatment from said computed significant value or values and from one or more values taken by the characteristic ($Cd_{in}$) in the fresh treatment liquid.

In a 4th aspect according to any one of the preceding aspects said reference portion (200) has a duration which is less than 70% compared to the duration of the entire downstream perturbation.

In a 5th aspect according to any one of the preceding aspects said reference portion (200) has a duration which is less than 50% compared to the duration of the entire downstream perturbation.

In a 6th aspect according to any one of the preceding aspects said control unit (10) is configured to set the duration of the said reference portion.

In a 7th aspect according to any one of the preceding aspects said control unit (10) is configured to allow setting of, via a user interface connected to the control unit, the duration of the said reference portion by a user acting on the user interface input.

In a 8th aspect according to any one of the preceding aspects said computing one or more significant values of said delayed variation of the characteristic ($Cd_{out}$) comprises determining the value ($Cd_{out}(n)$) of characteristic ($Cd_{out}$) in the spent liquid at time instant (n) by using as input to the characteristic mathematical model:

a) the values of characteristic ($Cd_{in}$) in the fresh treatment liquid at a plurality of time instants (n−1, n−2, n−3) preceding in time the time instant (n); or b) a mathematically calculated version of characteristic ($Cd_{in}$) in the fresh treatment liquid.

In a 9th aspect according to any one of the preceding aspects said computing one or more significant values of said delayed variation of the characteristic ($Cd_{out}$) comprises determining the value ($Cd_{out}(n)$) of characteristic ($Cd_{out}$) in the spent liquid at time instant (n) subsequent to said reference portion with the following recursive equation, which represents the parametric mathematical model in the time domain:

$$Cd_{out}(n)=a_0 \cdot Cd_{in}(n)+b_1 \cdot Cd_{out}(n-1)+b_2 \cdot Cd_{out}(n-2)+ b_m \cdot Cd_{out}(n-m),$$

wherein:

$Cd_{out}(n)$ is the calculated value of the outlet characteristic at time instant (n), $Cd_{in}(n)$ is the known value of the inlet characteristic at time instant (n), $Cd_{out}(n-1)$, $Cd_{out}(n-2)$, $Cd_{out}(n-m)$ are values of the outlet characteristic at preceding time instants (n−1, n-2, . . . n-m) prior to time instant (n) and recursively computed by means of the mathematical model, $a_0$, $b_1$, $b_2$, . . . , $b_m$ are constant parameters of the mathematical model, as estimated by using said measured values of the reference portion of the downstream variation.

In a 10th aspect according to any one of the preceding aspects said at least one mathematical model is a time invariant linear (LTI) model.

In a 11th aspect according to any one of the preceding aspects, in the frequency domain and using the z-Transform, the mathematical model is described by a transfer function H(z) having at least one zero and at least one pole.

In a 12th aspect according to the preceding aspect, the transfer function H(z) comprises a plurality of poles.

In a 13th aspect according to the preceding aspect, the transfer function H(z) comprises from 3 to 5 poles.

In a 14th aspect according to any one of the preceding three aspects, the transfer function H(z) is described by one of the following:

$$H(z)=Cd_{out}(z)/Cd_{in}(z)=a_0/(1-b_1 \cdot z^{-1}-b_2 \cdot z^{-2}-b_3 \cdot z^{-3}-b_4 \cdot z^{-4}-b_5 \cdot z^{-5}),$$

$$H(z)=Cd_{out}(z)/Cd_{in}(z)=a_0/(1-b_1 \cdot z^{-1}-b_2 \cdot z^{-2}-b_3 \cdot z^{-3}-b_4 \cdot z^{-4}),$$

$$H(z)=Cd_{out}(z)/Cd_{in}(z)=a_0/(1-b_1 \cdot z^{-1}-b_2 \cdot z^{-2}-b_3 \cdot z^{-3}), \text{ or}$$

$$H(z)=Cd_{out}(z)/Cd_{in}(z)=a_0/(1-b_1 \cdot z^{-1}-b_2 \cdot z^{-2}),$$

wherein $a_0$, $b_1$, $b_2$, $b_3$, $b_4$, $b_5$ are constant parameters of the model, as estimated by using said measured values of the reference portion of the downstream variation.

In a 15th aspect according to any one of the preceding aspects, the apparatus comprises:

a memory connected to the control unit (10) and storing one or more change setting procedures, each of said change setting procedures when executed by the control unit (10) configuring the control unit (10) to vary the value of the characteristic of the fresh dialysis liquid from said set value to a new set value, said control unit (10) being further configured to:

prevent execution of the change setting procedure(s) only until end measurement instant ($T_{END\_MEAS}$) at which the measurement of said plurality of values of the reference portion of said downstream variation in the characteristic ($Cd_{out}$) in the spent liquid has been completed.

In a 16th aspect according to the preceding aspect, the control unit is configured to allow execution of the change setting procedure(s) immediately after the end measurement instant ($T_{END\_MEAS}$).

In a 17th aspect according to the preceding aspect, the control unit (10) is further configured for:

receiving a total treatment time (T), and consecutively repeating at time intervals said task for the determination of the parameter (D, $Cb_{in}$, K, K-t/V) during the treatment time (T) such that a plurality of values of said parameter (D, $Cb_{in}$, K, K-t/V) indicative are correspondingly determined, allowing execution of one or more change setting procedures between two consecutive tasks.

In a 18th aspect according to any one of the preceding aspects, varying the value of the characteristic ($Cd_{in}$) in the fresh treatment liquid comprises imposing a change of the same from a first inlet value ($Cd_{in1}$) to a second inlet value ($Cd_{in2}$), which is kept constant for a prefixed time interval, thereby causing a corresponding change of the characteristic ($Cd_{out}$) in spent liquid from a respective first outlet value ($Cd_{out1}$) to a respective second outlet value ($Cd_{out2}$) defining said timely delayed downstream variation of the characteristic ($Cd_{out}$), wherein:

the reference portion of said downstream variation begins after the characteristic in the spent liquid changes from said first outlet value ($Cd_{out1}$) and lasts a period during which the characteristic either continuously increases or decreases without reaching the second outlet value ($Cd_{out2}$).

the control unit (10) is further configured to:

calculating the second outlet value ($Cd_{out2}$) of the characteristic ($Cd_{out}$) by using as input to the characteristic mathematical model the values of characteristic ($Cd_{in}$) in the fresh treatment liquid, or a mathematically calculated version of the characteristic ($Cd_{in}$) in the fresh treatment liquid, using the calculated second outlet value ($Cd_{out2}$) as significant value for the computation of at least one value of a parameter (D, $Cb_{in}$, K, K-t/V) indicative of the effectiveness of the extracorporeal blood treatment;

In a 19th aspect according to the preceding aspect wherein the reference portion of said downstream variation lasts a period during which the characteristic either continuously increases or decreases without reaching 80% of the second outlet value ($Cd_{out2}$).

In a 20th aspect according to any one of the preceding aspects from the 1st the 17th, varying the value of the characteristic ($Cd_{in}$) in the fresh treatment liquid comprises changing from a first inlet value ($Cd_{in1}$) to a second inlet value ($Cd_{in2}$), and then changing to a third inlet value ($Cd_{out3}$) thereby causing a corresponding time delayed downstream variation of the characteristic ($Cd_{out}$) in spent liquid comprising a change from a respective first outlet value ($Cd_{out1}$) to a respective second outlet value ($Cd_{out2}$) and then to a third out value ($Cd_{out3}$);

wherein:

the reference portion of the downstream variation begins after the characteristic in the spent liquid changes from said first outlet value ($Cd_{out1}$) and lasts a period shorter than a fraction of the duration of said downstream variation;

calculating, as significant value at least the third outlet value ($Cd_{out3}$) or both the second and the third outlet values ($Cd_{out2}$, $Cd_{out3}$) of the characteristic ($Cd_{out}$) by using as input to the characteristic mathematical model the values of characteristic ($Cd_{in}$) in the fresh treatment liquid, or a mathematically calculated version of the characteristic ($Cd_{in}$) in the fresh treatment liquid.

In a 21st aspect according to any one of the preceding aspects from the 1st to the 17th, varying the value of the characteristic ($Cd_{in}$) in the fresh treatment liquid comprises imposing an upstream perturbation in the characteristic of the fresh treatment liquid thereby causing a corresponding downstream perturbation of the characteristic ($Cd_{out}$) in spent liquid, wherein:

the reference portion of said downstream perturbation begins after the characteristic in the spent liquid changes from said first outlet value ($Cd_{out1}$) and lasts a prefixed period shorter than 60% of the duration of the downstream perturbation, and the control unit (10) is further configured to:

extrapolating a plurality of significant values of the characteristic ($Cd_{out}$), describing a remaining portion of the downstream perturbation consecutive to said reference portion, by using as input to the mathematical model the values of characteristic ($Cd_{in}$) in the fresh treatment liquid, or a mathematically calculated version of the characteristic ($Cd_{in}$) in the fresh treatment liquid, obtaining a calculated downstream perturbation from said extrapolated significant values, computing at least one value of a parameter (D, $Cb_{in}$, K, Kt/V) indicative of the effectiveness of the extracorporeal blood treatment by comparing the calculated downstream perturbation and the upstream perturbation.

In a 22nd aspect according to any one of the preceding aspects, said parameter comprises one selected in the group of:
- an effective dialysance for one or more substances of the treatment unit (D),
- an effective clearance for one or more substances of the treatment unit (K),
- a concentration of a substance in blood ($Cb_{in}$) upstream the blood treatment unit (2),
- a dialysis dose at time (t) after start of the treatment (K·t/V).

In a 23rd aspect according to any one of the preceding aspects from the 18th to the 22nd, the parameter comprises the effective dialysance (D) and wherein each computed value ($D_k$) of said parameter at each respective variation is obtained using the formula:

$$D_k = (Qd + WLR) \cdot [1 - (Cd_{out2} - Cd_{out1})]/(Cd_{in2} - Cd_{in1})$$

where:

$Cd_{out1}$ is the first outlet value taken by the characteristic in the spent dialysate line downstream of the secondary chamber in response to the change of characteristic ($Cd_{in}$) in the preparation line to said first inlet value $Cd_{in1}$, $Cd_{out2}$ is the second value taken by the characteristic in the spent dialysate line downstream of the secondary chamber in response to the change of characteristic ($Cd_{in}$) in the preparation line at said second inlet value ($Cd_{in2}$), $Cd_{in1}$, $Cd_{in2}$ are first and second inlet values taken by the characteristic (Cd) in the preparation line upstream of the secondary chamber, Qd is the fresh treatment liquid flow rate in the preparation line, WLR is the weight loss rate of a patient under treatment.

or the formula $$D_k = (Qd + WLR)[1(2 \times Cd_{out1} - Cd_{out2} - Cd_{out3})/(2 \times Cd_{in1} - Cd_{in2} - Cd_{in3})]$$

where:

$Cd_{out1}$ is the first outlet value taken by the characteristic in the spent dialysate line downstream of the secondary chamber in response to the change of characteristic $Cd_{in}$ in the preparation line to said first inlet value $Cd_{in1}$, $Cd_{out2}$ is the calculated second value (namely one of the significant values) which is representative of the value taken by the characteristic in the spent dialysate line downstream of the secondary chamber in response to the change of characteristic $Cd_{in}$ in the preparation line from said first inlet value $Cd_{in1}$ to said second inlet value $Cd_{in2}$, $Cd_{out3}$ is the calculated third value (namely one of the significant values) which is representative of the value taken by the characteristic in the spent dialysate line downstream of the secondary chamber in response to the change of characteristic $Cd_{in}$ in the preparation line from said second inlet value $Cd_{in2}$ to said third inlet value $Cd_{in3}$, $Cd_{in1}$, $Cd_{in2}$, $Cd_{in3}$ are first, second and third inlet values taken by the characteristic (Cd) in the preparation line upstream of the secondary chamber, Qd is the fresh treatment liquid flow rate in the preparation line, WLR is the weight loss rate of a patient under treatment.

In a 24th aspect according to any one of the preceding aspects, the control unit (10) is configured to:
- determine a downstream curve ($Cd_{out(t)}$) representative of the values taken by the characteristic ($Cd_{out}$) in the spent liquid,
- determine an angular deviation of a downstream baseline of the downstream curve ($Cd_{out(t)}$) with respect to the prescription baseline ($Cd_{set}$),
- compensate for said angular deviation by angularly rotating the downstream curve to obtain a corrected downstream curve ($Cd_{out-correct(t)}$).

In a 25th aspect according to the preceding aspect, the step of determining a downstream curve ($Cd_{out(t)}$) representative of the values taken by the characteristic ($Cd_{out}$) in the spent liquid comprises:
- using measured values across a time interval covering at least the entire downstream variation, or
- measuring values of the characteristic ($Cd_{out}$) in the spent liquid until the end of said reference portion, estimating the free parameters of the parametric mathematical model to identify the characteristic mathematical model, using said identified characteristic mathematical model to calculate the downstream curve ($Cd_{out(t)}$).

A 26th aspect concerns an apparatus for extracorporeal treatment of blood comprising:
- a blood treatment unit (2) having a primary chamber (3) and a secondary chamber (4) separated by a semipermeable membrane (5);
- a preparation line (19) having one end connected to an inlet of a secondary chamber (4) of the treatment unit (2) and configured to convey fresh treatment liquid to the secondary chamber (4), the fresh treatment liquid presenting a characteristic ($Cd_{in}$) which is either the conductivity in the fresh treatment liquid or the concentration of at least one substance (for instance sodium or calcium or potassium) in the fresh treatment liquid;
- a spent dialysate line (13) having one end connected to an outlet of said secondary chamber (4) and configured to remove spent liquid from the secondary chamber (4), the spent liquid presenting a characteristic ($Cd_{out}$) which is either the conductivity in the fresh treatment liquid or the concentration of at least one substance (for instance sodium or calcium or potassium) in the fresh treatment liquid;
- a control unit (10) configured for commanding execution of a task for determination of a parameter indicative of the effectiveness of the extracorporeal blood treatment, said task comprising the following steps:
  - causing an upstream variation of the value of the characteristic ($Cd_{in}$) in the fresh treatment liquid with respect to said prescription baseline ($Cd_{set}$) thereby causing a corresponding and timely delayed downstream variation of the same characteristic ($Cd_{out}$) in the spent liquid flowing in the spent dialysate line (13);

measuring a plurality of values taken by said downstream variation of the characteristic ($Cd_{out}$) in the spent liquid;

determine a downstream curve ($Cd_{out(t)}$) representative of the measured values taken by the characteristic ($Cd_{out}$) in the spent liquid, determine an angular deviation of a downstream baseline of the downstream curve ($Cd_{out(t)}$) with respect to the prescription baseline ($Cd_{set}$), compensate for said angular deviation by angularly rotating the downstream curve to obtain a corrected downstream curve ($Cd_{out\text{-}correct(t)}$), estimating at least one value of a parameter (D, $Cb_{in}$, K, K-t/V) indicative of the effectiveness of the extracorporeal blood treatment by using one or more values of said corrected downstream curve and one or more values taken by the characteristic ($Cd_{in}$) in the fresh treatment liquid.

In a 27th aspect according to any one of the preceding aspects, the control unit (10) is configured to:

determine a downstream curve ($Cd_{out(t)}$) representative of the values taken by the characteristic ($Cd_{out}$) in the spent liquid, analyze a frequency spectrum of the downstream curve ($Cd_{out(t)}$), filter out harmonics of said frequency spectrum of the downstream curve ($Cd_{out(t)}$) lying at frequencies higher than a prefixed threshold to eliminate noise and undesired perturbations possibly present in the downstream curve and obtain a corrected downstream curve ($Cd_{out\text{-}correct(t)}$);

wherein the step of determining a downstream curve ($Cd_{out(t)}$) representative of the values taken by the characteristic ($Cd_{out}$) in the spent liquid comprises:

using measured values across a time interval covering at least the entire downstream variation, or measuring values of the characteristic ($Cd_{out}$) in the spent liquid until the end of said reference portion, estimating the free parameters of the parametric mathematical model to identify the characteristic mathematical model, using said identified characteristic mathematical model to calculate the downstream curve ($Cd_{out(t)}$).

In a 28th aspect according to any one of the preceding aspects, the control unit (10) is further configured for: storing a plurality of mathematical models each of which puts into relation the characteristic ($Cd_{in}$) in the fresh treatment liquid with the characteristic ($Cd_{out}$) in the spent liquid;

selecting the mathematical model to be used for computing the at least one significant value of said downstream variation based at least on one selected in the group of the shape of said upstream variation and the type of blood treatment unit (2) used by the apparatus.

A 29th aspect concerns a method for determining an effectiveness parameter which may be used in and apparatus for extracorporeal treatment of blood comprising:

a blood treatment unit (2) having a primary chamber (3) and a secondary chamber (4) separated by a semipermeable membrane (5);

a preparation line (19) having one end connected to an inlet of a secondary chamber (4) of the treatment unit (2) and configured to convey fresh treatment liquid to the secondary chamber (4), the fresh treatment liquid presenting a characteristic ($Cd_{in}$) which is either the conductivity in the fresh treatment liquid or the concentration of at least one substance (for instance sodium or calcium or potassium) in the fresh treatment liquid;

a spent dialysate line (13) having one end connected to an outlet of said secondary chamber (4) and configured to remove spent liquid from the secondary chamber (4), the spent liquid presenting a characteristic ($Cd_{out}$) which is either the conductivity in the fresh treatment liquid or the concentration of at least one substance (for instance sodium or calcium or potassium) in the fresh treatment liquid;

wherein the method comprises the following steps:

causing an upstream variation of the value of the characteristic ($Cd_{in}$) in the fresh treatment liquid with respect to said prescription baseline ($Cd_{set}$) thereby causing a corresponding and timely delayed downstream variation of the same characteristic ($Cd_{out}$) in the spent liquid flowing in the spent dialysate line (13);

measuring a plurality of values taken by said downstream variation of the characteristic ($Cd_{out}$) in the spent liquid;

determine a downstream curve ($Cd_{out(t)}$) representative of the measured values taken by the characteristic ($Cd_{out}$) in the spent liquid, determine an angular deviation of a downstream baseline of the downstream curve ($Cd_{out(t)}$) with respect to the prescription baseline ($Cd_{set}$), compensate for said angular deviation by angularly rotating the downstream curve to obtain a corrected downstream curve ($Cd_{out\text{-}correct(t)}$), estimating at least one value of a parameter (D, $Cb_{in}$, K, K-t/V) indicative of the effectiveness of the extracorporeal blood treatment by using one or more values of said corrected downstream curve and one or more values taken by the characteristic ($Cd_{in}$) in the fresh treatment liquid.

A 30th aspect concerns a method for determining an effectiveness parameter which may be used in and apparatus for extracorporeal treatment of blood comprising:

a blood treatment unit (2) having a primary chamber (3) and a secondary chamber (4) separated by a semipermeable membrane (5);

a preparation line (19) having one end connected to an inlet of a secondary chamber (4) of the treatment unit (2) and configured to convey fresh treatment liquid to the secondary chamber (4), the fresh treatment liquid presenting a characteristic ($Cd_{in}$) which is either the conductivity in the fresh treatment liquid or the concentration of at least one substance (for instance sodium or calcium or potassium) in the fresh treatment liquid;

a spent dialysate line (13) having one end connected to an outlet of said secondary chamber (4) and configured to remove spent liquid from the secondary chamber (4), the spent liquid presenting a characteristic ($Cd_{out}$) which is either the conductivity in the fresh treatment liquid or the concentration of at least one substance (for instance sodium or calcium or potassium) in the fresh treatment liquid;

wherein the method comprises the following steps:

using at least one parametric mathematical model which puts into relation the characteristic ($Cd_{in}$) in the fresh treatment liquid with the characteristic ($Cd_{out}$) in the spent liquid, said parametric mathematical model presenting a prefixed number of free parameters;

causing an upstream variation of the value of the characteristic ($Cd_{in}$) in the fresh treatment liquid with respect to said prescription baseline ($Cd_{set}$) thereby causing a corresponding and timely delayed downstream variation of the same characteristic ($Cd_{out}$) in the spent liquid flowing in the spent dialysate line (13);

measuring a plurality of values taken by a reference portion (200) of said downstream variation of the characteristic ($Cd_{out}$) in the spent liquid, said reference portion having duration shorter than the entire duration of the downstream variation;

estimating said free parameters of the at least one parametric mathematical model by means of said reference portion measured values and identifying one single characteristic mathematical model which puts into relation the characteristic ($Cd_{in}$) in the fresh treatment liquid with the characteristic ($Cd_{out}$) in the spent liquid;

computing at least one value of a parameter (D, $Cb_{in}$, K, K-t/V) indicative of the effectiveness of the extracorporeal blood treatment by using said characteristic mathematical model and one or more values taken by the characteristic ($Cd_{in}$) in the fresh treatment liquid.

The methods of the 29th and 30th aspects may be used adopting the apparatus of any one of aspects from the 1st to the 27th.

BRIEF DESCRIPTION OF THE DRAWINGS

Aspects of the invention are shown in the attached drawings, which are provided by way of non-limiting example, wherein.

DETAILED DESCRIPTION

Figure 1:
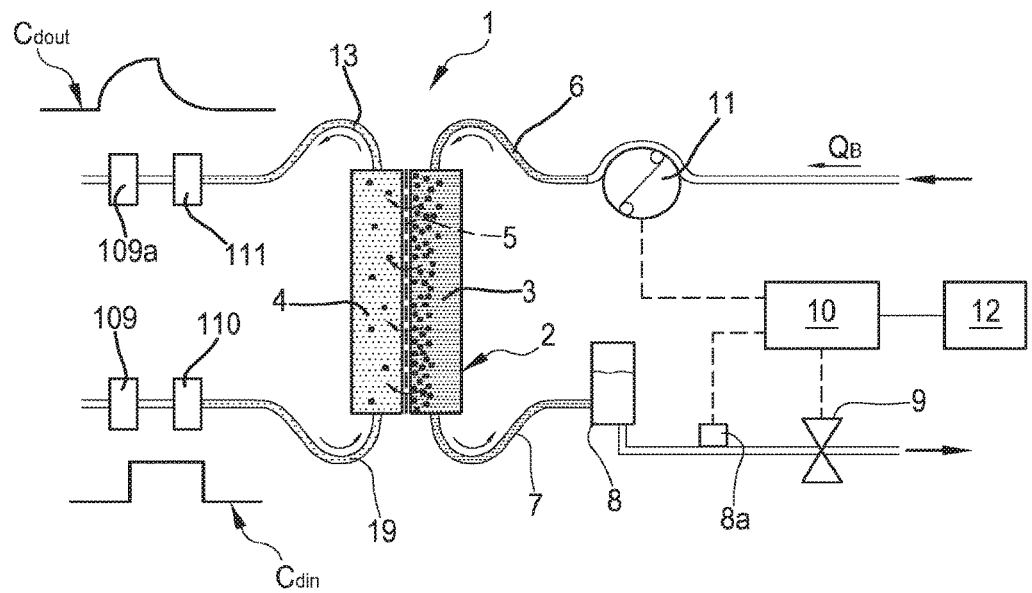
FIG. 1 shows a schematic diagram of a blood treatment apparatus according to one aspect of the invention.
Figure 2:
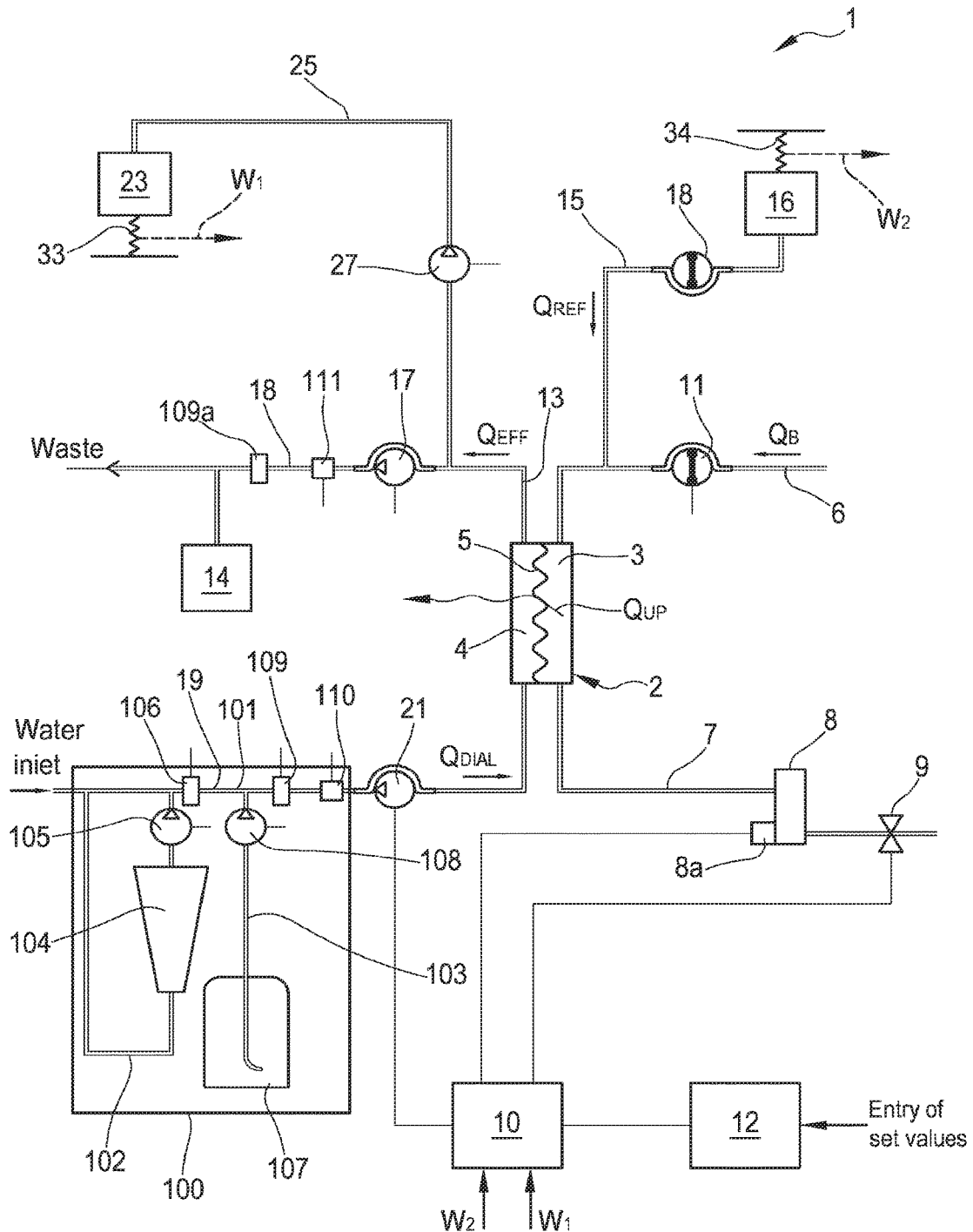
FIG. 2 shows a schematic diagram of an alternative embodiment of a blood treatment apparatus according to another aspect of the invention.
Figure 3:
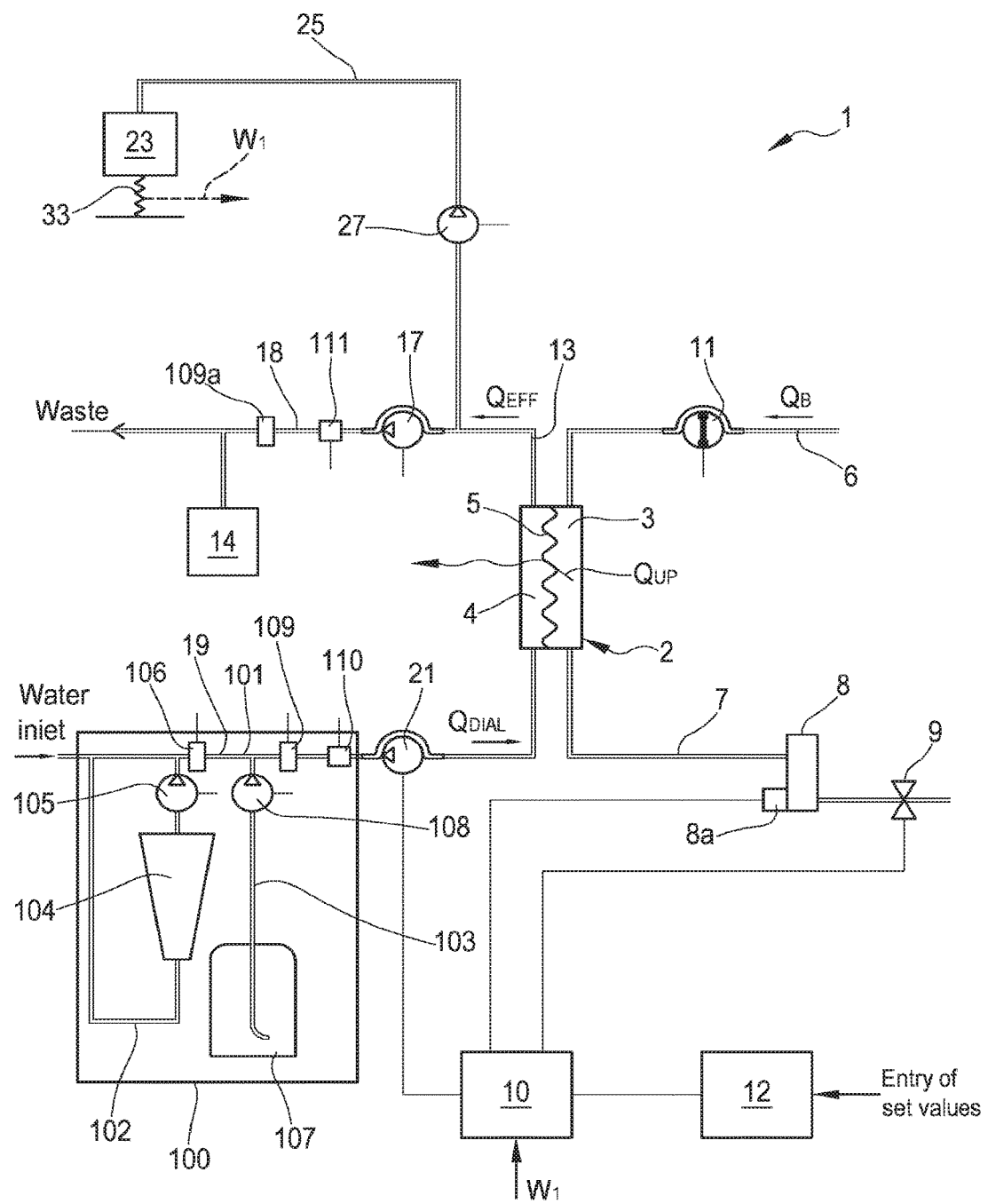
FIG. 3 shows a schematic diagram of another alternative embodiment of a blood treatment apparatus according to a further aspect of the invention.

Non-limiting embodiments of an apparatus 1 for extracorporeal treatment of blood—which may implement innovative aspects of the invention—are shown in FIGS. 1 to 3. FIG. 1 is a more schematic representation of the extracorporeal blood treatment apparatus 1, while FIGS. 2 and 3 represent, in greater detail, two possible non limiting embodiments of the apparatus 1.

The apparatus 1 may be configured to determine a parameter indicative of the effectiveness of the treatment delivered to a patient (here below also referred to as effectiveness parameter). The effectiveness parameter may be one of the following:

an effective dialysance for one or more substances of the treatment unit (D), e.g. electrolyte or sodium clearance;

an effective clearance for one or more substances of the treatment unit (K), e.g. urea clearance;

a concentration of a substance in blood (Cbin) upstream the blood treatment unit, e.g. sodium concentration in the blood upstream the treatment unit;

a dialysis dose delivered until a certain point in time after start of the treatment (K–t/V), where K is clearance, t represents the time interval from start of treatment until the point in time, and V represents a reference volume characteristic of the patient.

Note that a parameter proportional to one of the above parameters or known function of one or more of the above parameters may alternatively be used as 'effectiveness' parameter.

In below description and in FIGS. 1 to 3 same components are identified by same reference numerals.

In FIG. 1 it is represented an apparatus for the extracorporeal treatment of blood 1 comprising a treatment unit 2 (such as an hemofilter, an ultrafilter, an hemodiafilter, a dialyzer, a plasmafilter and the like) having a primary chamber 3 and a secondary chamber 4 separated by a semi-permeable membrane 5; depending upon the treatment, the membrane of the filtration unit may be selected to have different properties and performances. A blood withdrawal line 6 is connected to an inlet of the primary chamber 3, and a blood return line 7 is connected to an outlet of the primary chamber 3. In use, the blood withdrawal line 6 and the blood return line 7 are connected to a needle or to a catheter or other access device (not shown) which is then placed in fluid communication with the patient vascular system, such that blood may be withdrawn through the blood withdrawal line, flown through the primary chamber and then returned to the patient's vascular system through the blood return line. An air separator, such as a bubble trap 8, may be present on the blood return line; moreover, a safety clamp 9 controlled by a control unit 10 may be present on the blood return line downstream the bubble trap 8. A bubble sensor 8a, for instance associated to the bubble trap 8 or coupled to a portion of the line 7 between bubble trap 8 and clamp 9 may be present: if present, the bubble sensor is connected to the control unit 10 and sends to the control unit 10 signals for the control unit 10 to cause closure of the clamp 9 in case one or more bubbles above certain safety thresholds are detected. The blood flow through the blood lines is controlled by a blood pump 11, for instance a peristaltic blood pump, acting either on the blood withdrawal line or on the blood return line.

An operator may enter a set value for the blood flow rate $Q_B$ through a user interface 12 and the control unit 10, during treatment, is configured to control the blood pump based on the set blood flow rate. The control unit 10 may comprise a digital processor (CPU) and a memory (or memories), an analogical type circuit, or a combination thereof as explained in greater detail in below section dedicated to the 'control unit 10'.

An effluent fluid line or spent dialysate line 13 is connected, at one end, to an outlet of the secondary chamber 4 and, at its other end, to a waste which may be a discharge conduit or an effluent fluid container collecting the fluid extracted from the secondary chamber. A fresh dialysis fluid line 19 is connected to the inlet of the secondary chamber 4 and supplies fresh dialysate to from a source to said second chamber. Conductivity or concentration sensors 109, 109*a* are respectively positioned on the fresh dialysis fluid line 19 and on the spent dialysate line 13. Concentration or conductivity sensor 109 is configured for detecting the conductivity or the concentration for one substance of for a group of substances—identified as $Cd_{in}$—in the fresh dialysis fluid line 19. Concentration or conductivity sensor 109*a* is configured for detecting the conductivity or the concentration for one substance of for a group of substances—identified as $Cd_{out}$—in the spent dialysate line 19.

Figure 7:
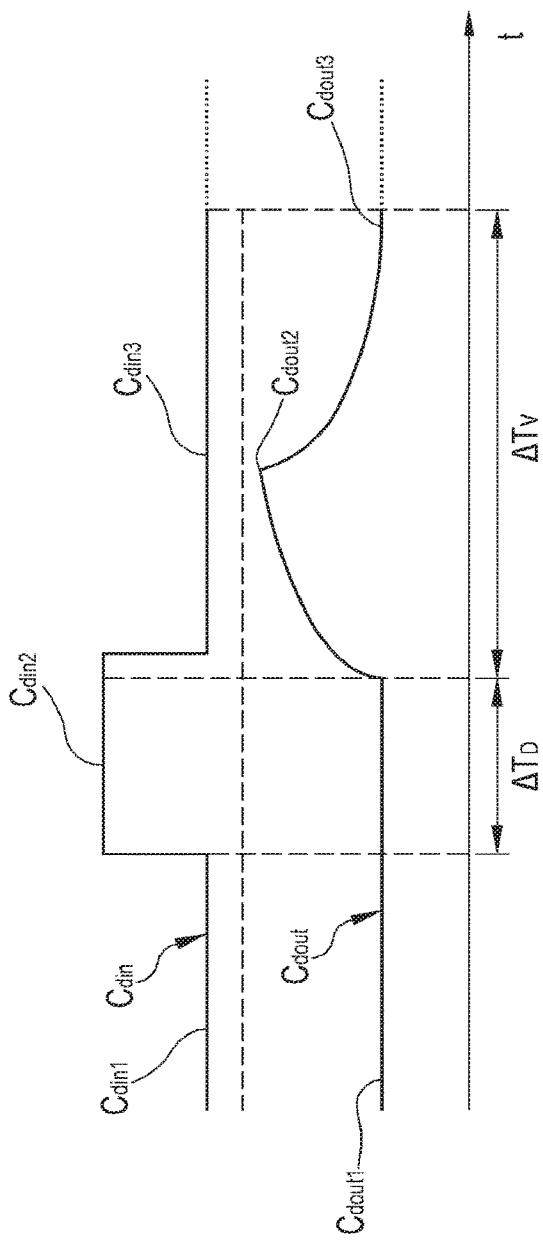
FIGS. 7 and 8 show a conductivity (or concentration) vs. time diagram in the fresh and in the spent dialysate line wherein the conductivity (or concentration) variation in the fresh dialysate line is in the form of a relatively short step.

FIG. 2 shows an apparatus 1 configured to deliver any one of treatments like ultrafiltration and hemodialysis and hemodiafiltration. The apparatus of FIG. 2 comprises all the features described above in connection with FIG. 1, which are identified in FIG. 2 with same reference numerals. Furthermore, in the apparatus of FIG. 2, other features of a possible embodiment of the apparatus 1 are schematically shown: an effluent fluid pump 17 that operates on the effluent fluid line under the control of control unit 10 to regulate the flow rate $Q_{eff}$ across the effluent fluid line. The apparatus 1 may also include an ultrafiltration line 25 branching off the effluent line 13 and provided with a respective ultrafiltration pump 27 also controlled by control unit 10. The embodiment of FIG. 2 presents a pre-dilution fluid line 15 connected to the blood withdrawal line: this line 15 supplies replacement fluid from an infusion fluid container 16 connected at one end of the pre-dilution fluid line. Although in FIG. 2 a container 16 is shown as the source of infusion fluid, this should not be interpreted in a limitative manner: indeed, the infusion fluid may also come from an on line preparation section 100 part of the apparatus 1. Note that alternatively to the pre-dilution fluid line the apparatus of FIG. 1 may include a post-dilution fluid line (not shown in FIG. 2) connecting an infusion fluid container to the blood return line. Finally, as a further alternative (not shown in FIG. 2) the apparatus of FIG. 2 may include both a pre-dilution and a post infusion fluid line: in this case each infusion fluid line may be connected to a respective infusion fluid container or the two infusion fluid lines may receive infusion fluid from a same source of infusion fluid such as a same infusion fluid container. Once again, the source of infusion fluid may alternatively be an online preparation section part of the apparatus 1 (similar to the device 100 described herein below) supplying fluid to the post and/or pre dilution lines. Furthermore, an infusion pump 18 operates on the infusion line 15 to regulate the flow rate $Q_{rep}$ through the infusion line. Note that in case of two infusion lines (pre-dilution and post-dilution) each infusion line may be provided with a respective infusion pump. The apparatus of FIG. 2, which includes a dialysis fluid line 19 connected at one end with a water inlet and at its other end with the inlet of the secondary chamber 4 of the filtration unit for supplying fresh dialysis liquid to the secondary chamber 4; a dialysis fluid pump 21 is operative on the dialysis liquid fluid line 19 under the control of said control unit 10, to supply fluid from the dialysis liquid container to the secondary chamber at a flow rate $Q_{dial}$. The dialysis fluid pump 21, the ultrafiltration pump 27, the concentrate pumps 105 and 108, the infusion fluid pump 15 and the effluent fluid pump 17 are operatively connected to the control unit 10 which controls the pumps as it will be in detail disclosed herein below. An initial tract of line 19 links the haemodialyser or hemodiafilter 2 to a device 100, for preparing the dialysis liquid, which also includes a further tract of said line 19. The device 100 comprises a main line 101, the upstream end of which is designed to be connected to a supply of running water. Connected to this main line 101 are a first secondary line 102 and a second secondary line 103. The first secondary line 102, which may be looped back onto the main line 101, is provided with a connector configured for fitting a container 104, such as a bag or cartridge or other container, containing sodium bicarbonate in granule form (alternatively a concentrate in liquid form may be used). Line 102 is furthermore equipped with a concentrate pump 105 for metering the sodium bicarbonate into the dialysis liquid: as shown in FIG. 7 the pump may be located downstream of the container 104. The operation of the pump 105 is determined by the comparison between 1) a conductivity set point value for the solution forming at the junction of the main line 101 and the first secondary line 102 and 2) the value of the conductivity of this mixture measured by means of a first conductivity probe 106 located in the main line 101 immediately downstream of the junction between the main line 101 and the first secondary line 102. The free end of the secondary line 103 is intended to be immersed in a container 107 for a concentrated saline solution, e.g. containing sodium chloride, calcium chloride, magnesium chloride and potassium chloride, as well as acetic acid. The secondary line 103 is equipped with a pump 108 for metering sodium into the dialysis liquid, the operation of which pump depends on the comparison between 1) a second conductivity set point value for the solution forming at the junction of the main line 101 and the second secondary line 103 and 2) the value of the conductivity of this solution measured by means of a second conductivity probe 109 located in the main line 12 immediately downstream of the junction between the main line 12 and the secondary line 103. Note that as an alternative, instead of conductivity sensors concentration sensors may in principle be used. Moreover, the specific nature of the concentrates contained in containers 104 and 107 may be varied depending upon the circumstances and of the type of dialysis fluid to be prepared.

The control unit 10 is also connected to the user interface 12, for instance a graphic user interface, which receives operator's inputs and displays the apparatus outputs. For instance, the graphic user interface 12 may include a touch screen, a display screen and hard keys for entering user's inputs or a combination thereof.

The embodiment of FIG. 3 shows an alternative apparatus 2 designed for delivering any one of treatments like hemodialysis and ultrafiltration. The apparatus of FIG. 3 includes the same components described for the apparatus of FIG. 1. In the apparatus shown in FIG. 3 the same components described for the embodiment of FIG. 2 are identified by same reference numerals and thus not described again. In practice, differently from the hemodiafiltration apparatus of FIG. 2, the apparatus of FIG. 3 does not present any infusion line.

In each one of the above described embodiments, flow sensors 110, 111 (either of the volumetric or of the mass type) may be used to measure flow rate in each of the lines. Flow sensors are connected to the control unit 10. In the example of FIG. 2 where the infusion line 15 and the ultrafiltration line 25 lead to a respective bag 16, 23, scales may be used to detect the amount of fluid delivered or collected. For instance, the apparatus of FIG. 2 includes a first scale 33 operative for providing weight information $W_1$ relative to the amount of the fluid collected in the ultrafiltration container 23 and a second scale 34 operative for providing weight information $W_2$ relative to the amount of the fluid supplied from infusion container 16. In the embodiment of FIG. 3, the apparatus includes a first scale 33 operative for providing weight information $W_1$ relative to the amount of the fluid collected in the ultrafiltration container 23. The scales are all connected to the control unit 10 and provide said weight information $W_i$ for the control unit 10 to determine the actual quantity of fluid in each container as well as the actual flow rate of fluid supplied by, or received in, each container. In the example of FIG. 1 there is no dedicated ultrafiltration line and the total amount of ultrafiltration is determined by the difference of the flow rates detected by sensors 110 and 111. The control unit 10 is configured to act on appropriate actuators, such as pumps, present on lines 13 and 19 and—using the information concerning the difference of flow rates as detected by sensors 110, 111—to make sure that a prefixed patient fluid removal is achieved in the course of a treatment time T, as required by the prescription provided to the control unit 10, e.g. via user interface 12.

In the example of FIGS. 2 and 3, in order to control the fluid balance between the quantity of fluid supplied to the secondary chamber 4 and the quantity of fluid extracted from the secondary chamber, the flow-meters 110, 111 positioned on the fresh dialysate line and on the waste line 13 provide the control unit 10 with signals indicative of the flow of fluid through the respective lines and the scale or scales provide weight information which allow the control unit 10 to derive the flow rate through the ultrafiltration line 25 and, if present, through the infusion line 15. The control unit 10 is configured to control at least pumps 17, 21 and 27 (in case of FIG. 2 also pump 18) to make sure that a prefixed patient fluid removal is achieved in the course of a treatment time T, as required by the prescription provided to the control unit 10, e.g. via user interface 12. Note that other fluid balance systems may be used: for instance in case the apparatus includes a container as source of fresh dialysis fluid and a container to collect waste, then scales may be used to detect the amount of fluid delivered or collected by each container and then inform the control unit 10 accordingly. As a further alternative, systems based on volumetric control may be used where the fresh dialysis liquid line 19 and the waste line 13 are connected to a balance chamber system assuring that—at each instant—the quantity of liquid flowing into line 19 is identical to the quantity of fluid exiting from line 13.

From a structural point of view one or more, containers 104, 107, 14, 16, 23 may be disposable plastic containers. The blood lines 6, 7 lines and the filtration unit may also be plastic disposable components which may be mounted at the beginning of the treatment session and then disposed of at the end of the treatment session. Pumps, e.g. peristaltic pumps or positive displacement pumps, have been described as means for regulating fluid flow through each of the lines; however, it should be noted that other flow regulating means may alternatively be adopted such as for example valves or combinations of valves and pumps. The scales may comprise piezoelectric sensors, or strain gauges, or spring sensors, or any other type of transducer able to sense forces applied thereon. As already explained, the conductivity sensors may be replaced by concentration sensors.

Determination of the Effectiveness Parameter

As mentioned at the beginning of the detailed description, the apparatus 1 is capable of determining an effectiveness parameter. In this regard, the control unit 10 of the apparatus 1 is configured for commanding execution of a number of procedures including a task specifically devoted to the determination of the parameter indicative of the effectiveness of the extracorporeal blood treatment. The task devoted to determination of the effectiveness parameter comprises the steps described herein below.

First, the control unit 10 is configured for receiving at least one prescription baseline $Cd_{set}$ for the characteristic $Cd_{in}$ in the fresh treatment liquid; the characteristic may be the concentration for one substance in the dialysis liquid (e.g. the sodium concentration, or the calcium concentration), or the concentration for a group of substances in the dialysis liquid (such as the electrolyte concentration) or the conductivity of the dialysis liquid. Furthermore, the set value for the prescription baseline may be either pre set in a memory connected to the control unit 10 or, alternatively, it may be entered by the user via user interface 12.

Although the prescription baseline is frequently a constant value, it may alternatively comprise a time-variable value which changes during treatment according to a prefixed law.

The control unit 10, acting on appropriate actuators such as pumps 21 and 17, causes circulation of dialysis fluid through lines 19 and 13 and through the secondary chamber 4 of the treatment unit 2. In greater detail, the control unit 10 is configured for causing fresh treatment liquid to flow in the preparation line 19 to the secondary chamber 4 with the characteristic being at said prescription baseline $Cd_{set}$: the characteristic at the baseline value may for instance be achieved by appropriately controlling the concentrate pumps 105, 108 of the preparation section 100. Furthermore, the control unit 10 is configured for reading the value of the characteristic in the spent dialysis fluid using sensor 109a. Depending upon the case, sensor 109a may for instance be a conductivity sensor, or a concentration sensor (sensitive to one or more substances).

The control unit 10 is also configured to receive at least one parametric mathematical model which puts into relation the characteristic $Cd_{in}$ in the fresh treatment liquid with the characteristic $Cd_{out}$ in the spent liquid. The parametric mathematical model, which mathematically describes the components interposed between the two sensors 109, 109a, may for instance be pre-stored in a memory connected to the control unit 10, or it may be transferred to said memory via user interface 12 or via other input means such as a data reader, or it may be remotely transmitted from a remote source. The parametric model mathematically models the portion of hydraulic circuit between the sensors 109 and 109a and presents a prefixed number of free parameters that are determined as described herein below in order to characterize the parametric mathematical model into one single model. In practice, the parametric mathematical model defines a family of mathematical models and is univocally characterized only once the parameters of the model are determined.

Figure 4:
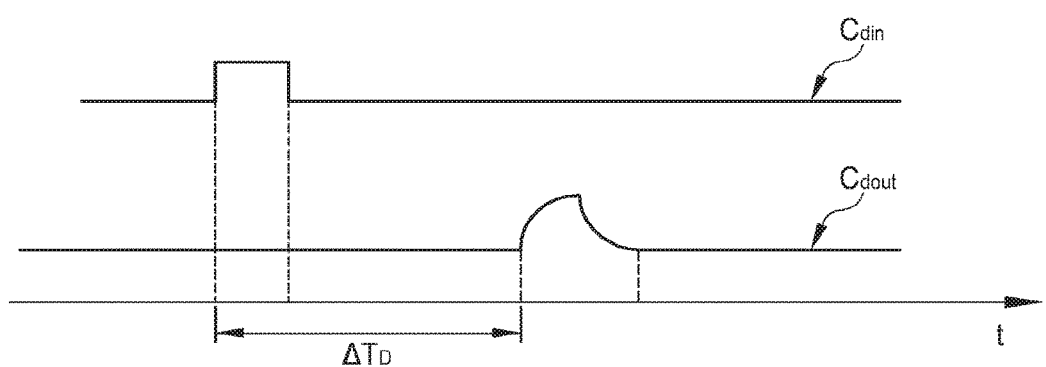
FIG. 4 shows a conductivity (or concentration) vs. time diagram showing the conductivity (or concentration) profile in the fresh and in the spent dialysate line, according to another aspect of the invention.

In addition to command the circulation of dialysis liquid in lines 19 and 13, the control unit 10, e.g. by acting one or more concentrate pumps 105, 108, causes an upstream variation of the value of the characteristic $Cd_{in}$ in the fresh treatment liquid with respect to said prescription baseline $Cd_{set}$ and then re-establishes the characteristic $Cd_{in}$ in the fresh treatment liquid to said prescription baseline $Cd_{set}$. Note that the alteration of the characteristic may be made using any means able to momentarily change the characteristic of the dialysis liquid, e.g. the conductivity or the concentration for one or more substances in the fresh dialysis fluid: for instance, a bolus pump configured to inject a predefined bolus of saline may be used for this purpose. The upstream variation causes a corresponding and timely delayed downstream variation of the same characteristic $Cd_{out}$ in the spent liquid flowing in the spent dialysate line: FIG. 4 schematically shows the time delay $\Delta T_D$ between the upstream variation and the downstream variation; the time delay which is also referred to as hydraulic delay depends upon the components such as tubing and second chamber interposed between the sensor 109 and the sensor 109a. The time delay $\Delta T_D$ between the upstream variation and the downstream variation is also shown in FIGS. 5, 6, 7, 8.

In order to determine the parameters of the parametric mathematical model, the control unit 10 is configured to receive, e.g. from sensor 109a, measures of a plurality of values taken by a reference portion 200 of the downstream variation of the characteristic $Cd_{out}$ in the spent liquid. The measured values taken by the reference portion 200 of the variation in the characteristic $Cd_{out}$ may be measured by first identifying the initiation of a ramp-up or of a ramp-down portion of the downstream variation with respect to a respective baseline value of the same characteristic $Cd_{out}$ in the spent liquid, and then by measuring the plurality of values, as values taken by said ramp-up portion or ramp-down portion of said downstream variation.

Figure 5:
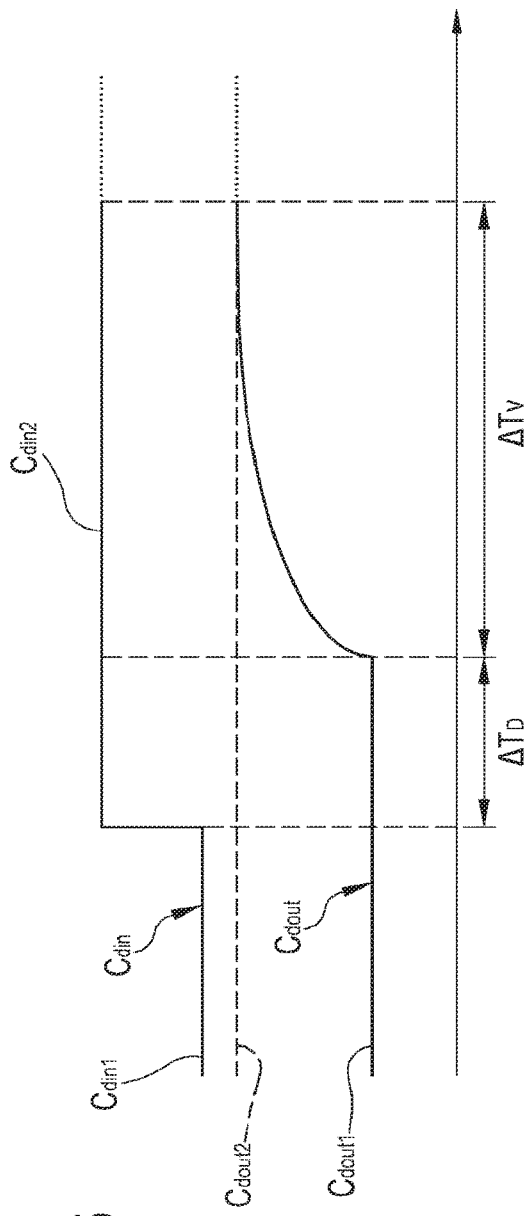
FIGS. 5 and 6 show a conductivity (or concentration) vs. time diagram in the fresh and in the spent dialysate line wherein the conductivity (or concentration) variation in the fresh dialysate line is in the form of a relatively long step.
Figure 6:
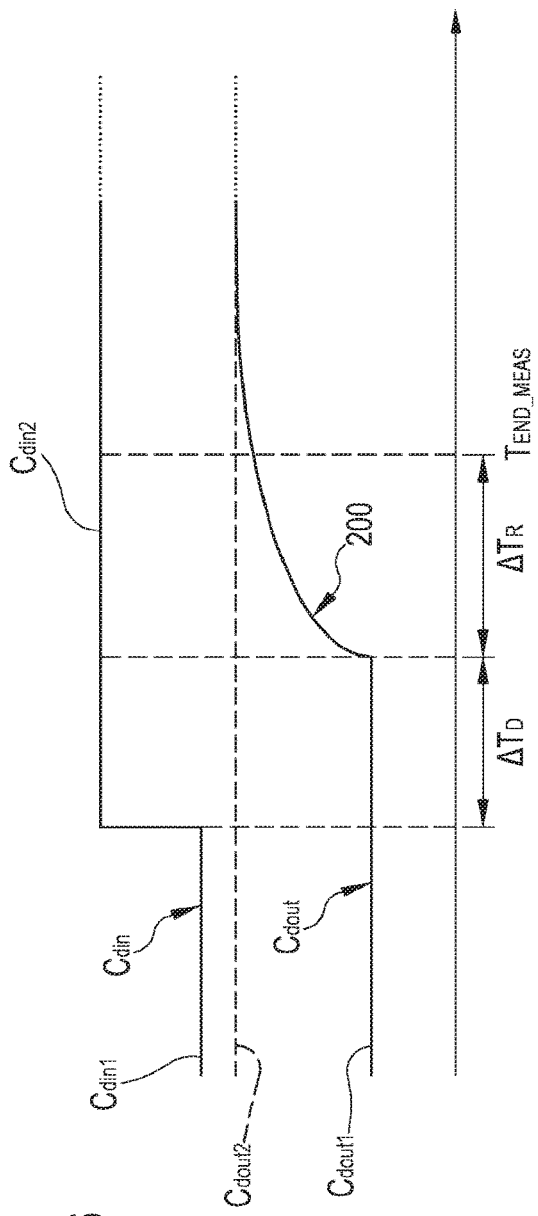

According to an aspect of the invention, the reference portion 200 which is used by the control unit 10 to characterize the mathematical model has a duration $\Delta T_R$ significantly shorter than the entire duration $\Delta T_v$ of the downstream variation: duration $\Delta T_R$ may be less than 70% and optionally less than 50% of duration $\Delta T_v$. This is visible e.g. in FIGS. 5 and 6: FIG. 5 shows the duration $\Delta T_v$ of the entire downstream variation which certain conventional systems have to wait in order to calculate the effectiveness parameter, while FIG. 6 shows the much shorter interval $\Delta T_R$ necessary to characterize the mathematical model and then calculate the effectiveness parameter. More in detail, according to an aspect of the invention, the control unit 10 characterizes the mathematical model without having to wait for the entire interval $\Delta T_v$ by estimating the free parameters of the parametric mathematical model using measured values taken by the reference portion thereby identifying one single characteristic mathematical model using measured values taken during time interval $\Delta T_R$ which is much shorter than $\Delta T_v$.

Once the parameters of the model have been determined, the control unit 10 has the characteristic mathematical model and may compute the value of the effectiveness parameter supplying as input to the characteristic mathematical model one or more values taken by the characteristic $Cd_{in}$ in the fresh treatment liquid. In other words with use of the parametric mathematical model and with the characterization of the same by means of measured values taken by the characteristic $Cd_{out}$ during $\Delta T_R$, it is possible to then calculate the effectiveness parameter with no need to take measures during the entire downstream variation, thus shortening the time during which control of the characteristic (e.g. concentration or conductivity of the dialysis liquid) should not be taken over by procedures other than the task for the determination of the effectiveness parameter. In other words the task for determining the effectiveness parameter should prevent execution of other procedures acting on the characteristic of the fresh dialysis liquid only until the end measurement instant $T_{END\_MEAS}$ represented in FIGS. 6, 8 and 9 which is the instant at which the measurement of said plurality of values of the reference portion of said downstream variation necessary for characterizing the model has been completed.

In order to calculate the effectiveness parameter, the control unit 10 may for instance first compute at least one significant value of said downstream variation of the characteristic $Cd_{out}$: the significant value of the downstream variation is a computed not measured value which, as shown in the example of FIG. 6, relates to a time subsequent to the duration of the reference portion, for instance it may represent an asymptotic value $Cd_{out2}$ that the downstream variation would take after a relatively long time. This value is computed by using the characteristic mathematical model providing one or more real or set values representative of the upstream variation; once the significant value $Cd_{out2}$ has been determined, the control unit 10 may compute at least one value of a parameter (D, $Cb_{in}$, K, K-t/V) indicative of the effectiveness of the extracorporeal blood treatment from said computed significant value and from one or more values taken by the characteristic $Cd_{in}$ in the fresh treatment liquid.

The computation of the at least one significant value or directly of the effectiveness parameter comprises determining the value $Cd_{out}(n)$ of characteristic $Cd_{out}$ in the spent liquid at time instant (n) by using as input to the mathematical model:

a) the measured values of characteristic $Cd_{in}$ in the fresh treatment liquid at a plurality of time instants (n−1, n−2, n−3) preceding in time the time instant (n), as measured for instance by sensor 109; or b) a mathematically calculated version of characteristic $Cd_{in}$ in the fresh treatment liquid; in this second case the input is a set curve or a number of set values which are fed as input to the mathematical model.

The mathematical model for instance a time invariant linear (LTI) model—may be represented in the time domain by the following recursive equation:

$$y(n)=a_0 \cdot u(n)+b_1 \cdot y(n-1)+b_2 \cdot y(n-2)+ \ldots b_m \cdot y(n-m),$$

Thus, the value $Cd_{out}(n)$ of characteristic $Cd_{out}$ in the spent liquid at time instant (n) subsequent to said reference portion is calculated with the following recursive equation:

$$Cd_{out}(n)=a_0 \cdot Cd_{in}(n)+b1 \cdot Cd_{out}(n-1)+b_2 \cdot Cd_{out}(n-2)+ \ldots b_m \cdot Cd_{out}(n-m),$$

wherein:

$Cd_{out}(n)$ is the calculated value of the outlet characteristic at time instant (n), $Cd_{in}(n)$ is the known value of the inlet characteristic at time instant (n), $Cd_{out}(n-1)$, $Cd_{out}(n-2)$, ..., $Cd_{out}(n-m)$ are values of the outlet characteristic at preceding time instants (n−1, n−2, ... n−m) prior to time instant (n) and recursively computed by means of the mathematical model.

$a_0, b_1, b_2, \ldots, b_m$ are constant parameters that characterize the mathematical model, as estimated by using said measured values of the reference portion of the downstream variation.

In the frequency domain and using the z-Transform—the mathematical model is described by a transfer function H(z) having at least one zero and at least one pole. In an embodiment, the transfer function H(z) comprises a plurality of poles, e.g. from 2 to 5 poles, and is described by one of the following:

$$H(z)=Cd_{out}(z)/Cd_{in}(z)=a_0/(1-b_1 \cdot z^{-1}-b_2 \cdot z^{-2}-b_3 \cdot z^{-3}-b_4 \cdot z^{-4}-b_5 \cdot z^{-5}),$$

$$H(z)=Cd_{out}(z)/Cd_{in}(z)=a_0/(1-b_1 \cdot z^{-1}-b_2 \cdot z^{-2}-b_3 \cdot z^{-3}-b_4 \cdot z^{-4}),$$

$$H(z)=Cd_{out}(z)/Cd_{in}(z)=a_0/(1-b_1 \cdot z^{-1}-b_2 \cdot z^{-2}-b_3 \cdot z^{-3}), \text{ or}$$

$$H(z)=Cd_{out}(z)/Cd_{in}(z)=a_0/(1-b_1 \cdot z^{-1}-b_2 \cdot z^{-2}),$$

wherein $a_0, b_1, b_2, b_3, b_4, b_5$ are constant parameters of the model, as estimated by using said measured values of the reference portion of the downstream variation.

FIGS. 5, 6 and 7, 8 respectively show two possible implementations of the invention. In FIGS. 5 and 6 the characteristic is altered from a first to a second value and kept at the second value for a relatively long time, while in FIGS. 7 and 8 the characteristic is kept at the second value for a relatively short time. More in detail, in the example of FIGS. 5 and 6, the value of the characteristic $Cd_{in}$ in the fresh treatment liquid is varied by imposing a change of the same from a first inlet value $Cd_{in1}$ to a second inlet value $Cd_{in2}$, which may be kept constant for a prefixed time interval of e.g. 3 to 10 minutes, thereby causing a corresponding change of the characteristic $Cd_{out}$ in spent liquid from a respective first outlet value $Cd_{out1}$ to a respective second outlet value $Cd_{out2}$ defining said timely delayed downstream variation of the characteristic $Cd_{out}$. In the example of FIGS. 5 and 6, the reference portion of the downstream variation begins after the characteristic in the spent liquid changes from said first outlet value $Cd_{out1}$ and lasts a period—for instance prefixed period $\Delta T_R$—during which the characteristic either continuously increases or decreases without reaching the second outlet value $Cd_{out2}$. In the example shown, during $\Delta T_R$ the characteristic $Cd_{out}$ does not reach a prefixed fraction, e.g. 80%, of the second outlet value $Cd_{out2}$. Moreover, there is no need to wait until the real value $Cd_{out2}$ is actually reached. Instead, the second outlet value $Cd_{out2}$ of the characteristic $Cd_{out}$ is calculated by using as input to the characteristic mathematical model the values of characteristic $Cd_{in}$ in the fresh treatment liquid, or a mathematically calculated version of the characteristic $Cd_{in}$ in the fresh treatment liquid.

Then, the calculated second outlet value $Cd_{out2}$ is used as significant value for the computation of at least one value of a parameter (D, $Cb_{in}$, K, K-t/V) indicative of the effectiveness of the extracorporeal blood treatment. In accordance with an aspect, if the parameter comprises is effective dialysance D, each computed value $D_k$ of the dialysance each respective variation is obtained using the formula:

$$D_k=(Qd+WLR)\cdot[1-(Cd_{out2}-Cd_{out1})]/(Cd_{in2}-Cd_{in1})$$

where:

$Cd_{out1}$ is the first outlet value taken by the characteristic in the spent dialysate line downstream of the secondary chamber in response to the change of characteristic $Cd_{in}$ in the preparation line to said first inlet value $Cd_{in1}$, $Cd_{out2}$ is the calculated second value (namely the significant value) which is representative of the value taken by the characteristic in the spent dialysate line downstream of the secondary chamber in response to the change of characteristic $Cd_{in}$ in the preparation line from said first inlet value $Cd_{in1}$ to said second inlet value $Cd_{in2}$, $Cd_{in1}$, $Cd_{in2}$ are first and second inlet values taken by the characteristic (Cd) in the preparation line upstream of the secondary chamber, Qd is the fresh treatment liquid flow rate in the preparation line, WLR is the weight loss rate of a patient under treatment.

Figure 8:
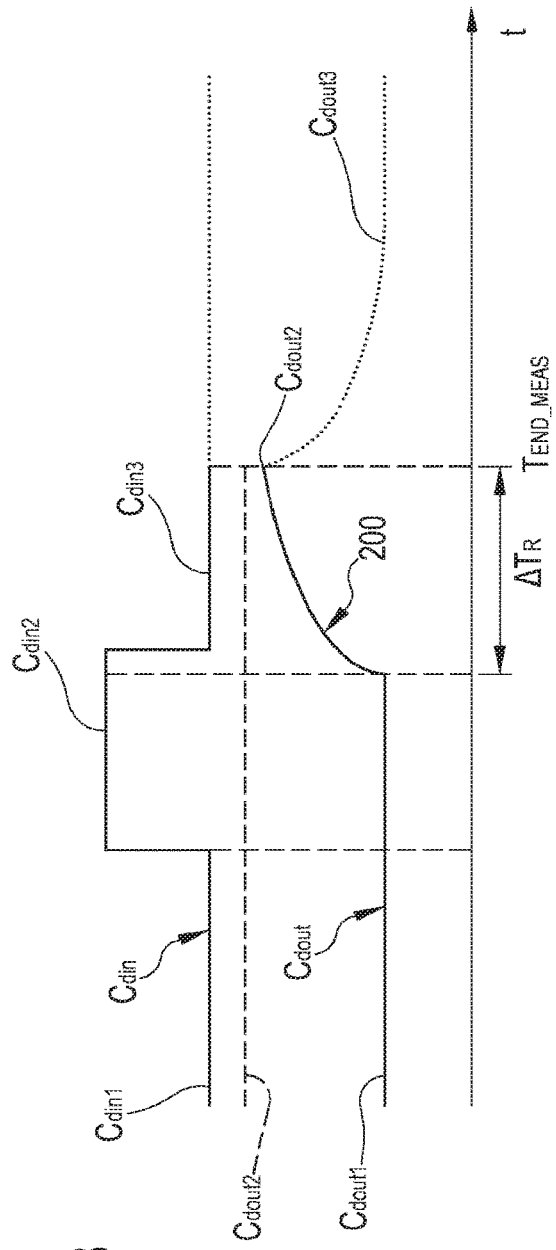

In FIGS. 7, 8 the upstream perturbation is shorter and the value of the characteristic $Cd_{in}$ in the fresh treatment liquid is varied by imposing a change of the same from a first inlet value $Cd_{in1}$ to a second inlet value $Cd_{in2}$, which may optionally be kept constant for a prefixed time interval of e.g. 1 to 2 minutes, and then a further change to a third inlet value $Cd_{out3}$ thereby causing a corresponding change of the characteristic $Cd_{out}$ in spent liquid from a respective first outlet value $Cd_{out1}$ to a respective second outlet value $Cd_{out2}$ and then back to a third value $Cd_{out3}$ to define said timely delayed downstream variation of the characteristic $Cd_{out}$. In the example of FIGS. 7 and 8, $Cd_{in1}$ is equal or close to $Cd_{in3}$. In case a short perturbation is used, the formula needed for the calculation of the effectiveness parameter requires more than simply the knowledge of one significant value such as $Cd_{out2}$. In the example of FIGS. 7 and 8, the reference portion of the downstream variation begins after the characteristic in the spent liquid changes from said first outlet value $Cd_{out1}$ and lasts a period—for instance prefixed period $\Delta T_R$—during which the characteristic either continuously increases or decreases. During $\Delta T_R$ the characteristic $Cd_{out}$ may or may not reach the second outlet value $Cd_{out2}$. In accordance with an aspect, there is no need to wait until $Cd_{out}$ reaches $Cd_{out2}$ and returns to the baseline value $Cd_{out3}$—Instead, the second and third $Cd_{out2}$ and $Cd_{out3}$ or at least the third outlet value $Cd_{out3}$ of the characteristic $Cd_{out}$ are/is calculated by using as input to the characteristic mathematical model the values of characteristic $Cd_{in}$ in the fresh treatment liquid, or a mathematically calculated version of the characteristic $Cd_{in}$ in the fresh treatment liquid.

Once the values $Cd_{out1}$, $Cd_{out2}$, $Cd_{out3}$ have been calculated, the effectiveness parameter may be determined based on these calculated values and on one or more inlet values of the conductivity, e.g. $Cd_{in1}$, $Cd_{in2}$, $Cd_{in3}$. For instance if dialysance is to be calculated, the following formula may be adopted:

$$D=(Qd+WLR)[1(2\times Cd_{out1}-Cd_{out2}-Cd_{out3})]/(2\times Cd_{in1}-Cd_{in2}-Cd_{in3})]$$

where:

$Cd_{out1}$ is the first outlet value taken by the characteristic in the spent dialysate line downstream of the secondary chamber in response to the change of characteristic $Cd_{in}$ in the preparation line to said first inlet value $Cd_{in1}$, $Cd_{out2}$ is the calculated second value (namely one of the significant values) which is representative of the value taken by the characteristic in the spent dialysate line downstream of the secondary chamber in response to the change of characteristic $Cd_{in}$ in the preparation line from said first inlet value $Cd_{in1}$ to said second inlet value $Cd_{in2}$, $Cd_{out3}$ is the calculated third value (namely one of the significant values) which is representative of the value taken by the characteristic in the spent dialysate line downstream of the secondary chamber in response to the change of characteristic $Cd_{in}$ in the preparation line from said second inlet value $Cd_{in2}$ to said third inlet value $Cd_{in3}$, $Cd_{in1}$, $Cd_{in2}$, $Cd_{in3}$ are first, second and third inlet values taken by the characteristic (Cd) in the preparation line upstream of the secondary chamber, Qd is the fresh treatment liquid flow rate in the preparation line, WLR is the weight loss rate of a patient under treatment.

Figure 9:
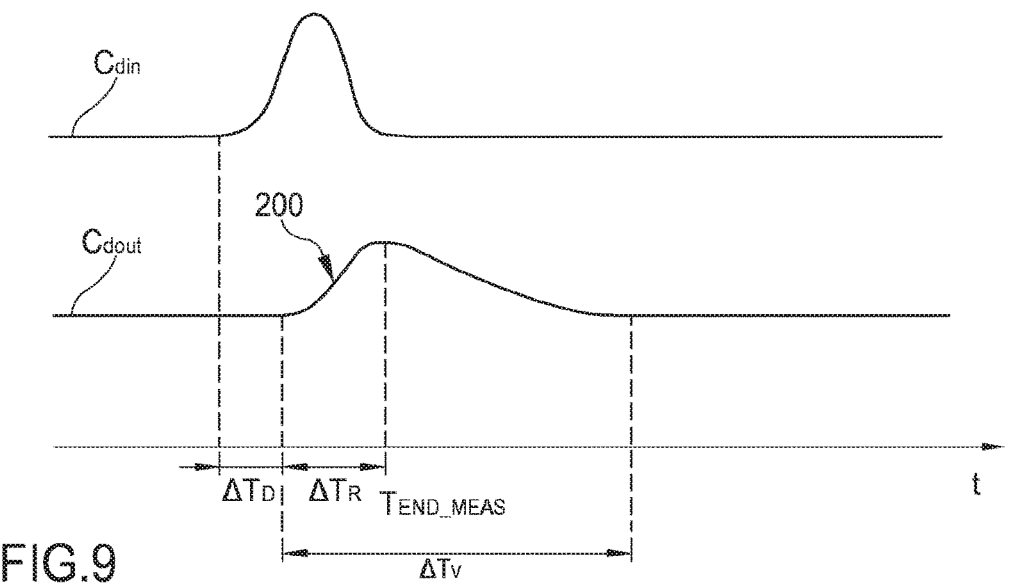
FIG. 9 shows a conductivity (or concentration) vs. time diagram in the fresh and in the spent dialysate line wherein the conductivity (or concentration) variation in the fresh dialysate line is in the form of pulse.

According to a further embodiment, see FIG. 9, varying the value of the characteristic $Cd_{in}$ in the fresh treatment liquid comprises imposing an upstream perturbation, which may be in the shape of a sinusoid or of a short peak, in the characteristic of the fresh treatment liquid thereby causing a corresponding downstream perturbation of the characteristic $Cd_{out}$ in spent liquid. The reference portion of said downstream perturbation begins after the characteristic in the spent liquid changes from said first outlet value $Cd_{out1}$ and lasts a prefixed period shorter than a fraction, e.g. 60% or even 50%, of the duration of the entire downstream perturbation. The control unit 10 determines in this case a plurality, e.g. 10 or more, of significant values of the characteristic $Cd_{out}$, describing a remaining portion of the downstream perturbation consecutive to said reference portion, by using as input to the mathematical model the values of characteristic $Cd_{in}$ in the fresh treatment liquid, or a mathematically calculated version of the characteristic $Cd_{in}$ in the fresh treatment liquid, thereby obtaining a calculated downstream perturbation from said extrapolated significant values. Then, using e.g. the formulas described in EP 0920877, the control unit computes at least one value of a parameter (D, $Cb_{in}$, K, Kt/V) indicative of the effectiveness of the extracorporeal blood treatment by comparing the calculated downstream perturbation and the upstream perturbation.

In accordance with a further aspect of the invention, the control unit 10 may also be configured to determine the baseline of the downstream curve representative of the values $Cd_{out(t)}$ taken over time by said characteristic in the spent dialysate line downstream of the secondary chamber. The baseline of the downstream curve $Cd_{out(t)}$ may be determined using measured values of the characteristic $Cd_{out}$ in the spent liquid or using a calculated curve representative of the downstream variation which has been previously determined using the characteristic mathematical model. In this second option only measured values of the characteristic $Cd_{out}$ in the spent liquid during said reference portion are used for the determination of the free parameters to identify the characteristic mathematical model; then using said identified characteristic mathematical model, a downstream curve $Cd_{out(t)}$ representative of the values taken by the characteristic $Cd_{out}$ in the spent liquid is mathematically determined and the baseline thereof identified.

Figure 10:
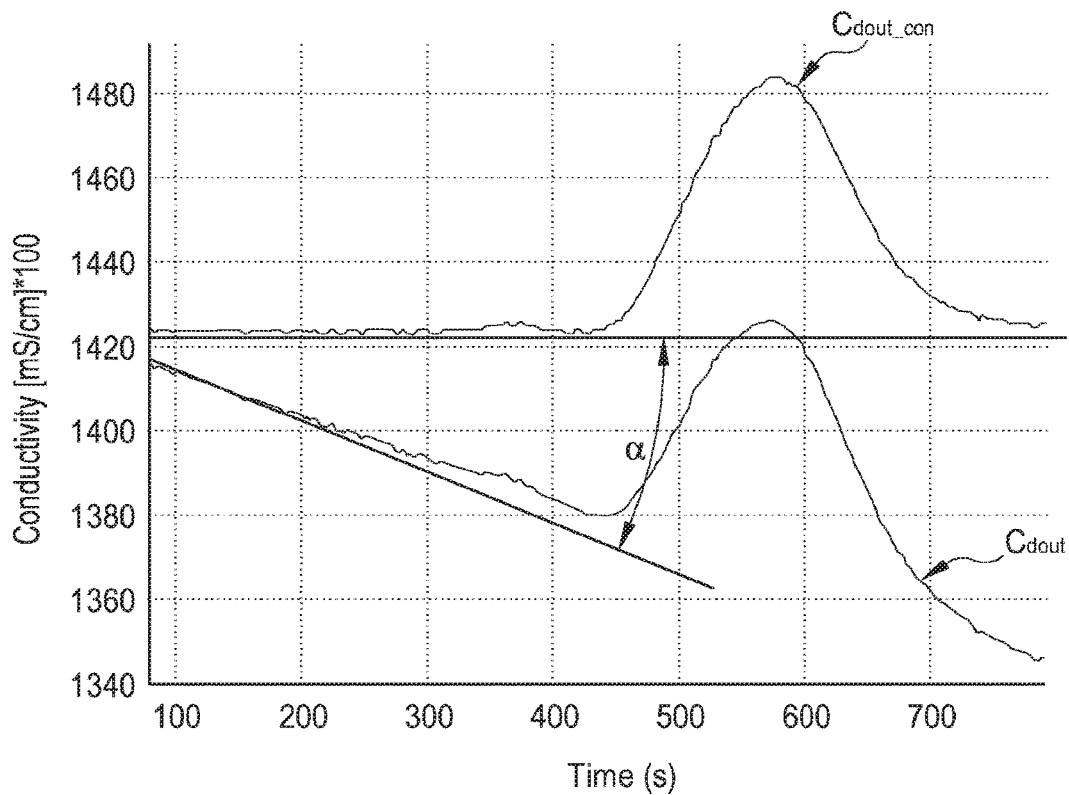
FIG. 10 is a diagram showing the outlet conductivity (or concentration) vs. time and schematically illustrating an angular correction of the conductivity (or concentration) baseline.

The control unit may be configured to determine an angular deviation a between the baseline of the downstream curve $Cd_{out(t)}$ with respect to the prescription baseline $Cd_{set}$, and to compensate for said angular deviation by angularly rotating the downstream curve to obtain a corrected downstream curve $Cd_{out-correct(t)}$, as shown in a the enlarged representation of FIG. 10.

According to a yet further aspect, the control unit 10 is configured to remove undesired noise and perturbation from the characteristic $Cd_{out}$. In accordance with an aspect, the control unit may receive measured values of the characteristic $Cd_{out}$ in the spent liquid during said reference portion, estimate the free parameters of the parametric mathematical model to identify the characteristic mathematical model, determine a downstream curve $Cd_{out(t)}$ representative of the values taken by the characteristic $Cd_{out}$ in the spent liquid using said identified characteristic mathematical model, analyze a frequency spectrum of the downstream curve $Cd_{out(t)}$, filter out harmonics of said frequency spectrum of the downstream curve $Cd_{out(t)}$ lying at frequencies higher than a prefixed threshold to eliminate noise and undesired perturbations possibly present in the downstream curve and obtain a corrected downstream curve $Cd_{out-correct(t)}$.

Although the above description referred to one single parametric mathematical model, the control unit 10 may further be configured for storing a plurality of mathematical models each of which puts into relation the characteristic ($Cd_{in}$) in the fresh treatment liquid with the characteristic ($Cd_{out}$) in the spent liquid. In this case the control unit may be configured for selecting the mathematical model to be used for computing the at least one significant value of said downstream variation based on certain factors such as for instance: the shape of the upstream variation (one mathematical model may be better suited for a long step perturbation while another model may more properly operate for a short sinusoidal change), the type of blood treatment unit used by the apparatus, whether or not particular hydraulic components are present in the circuit section between sensor 109 and sensor 109a.

Figure 11:
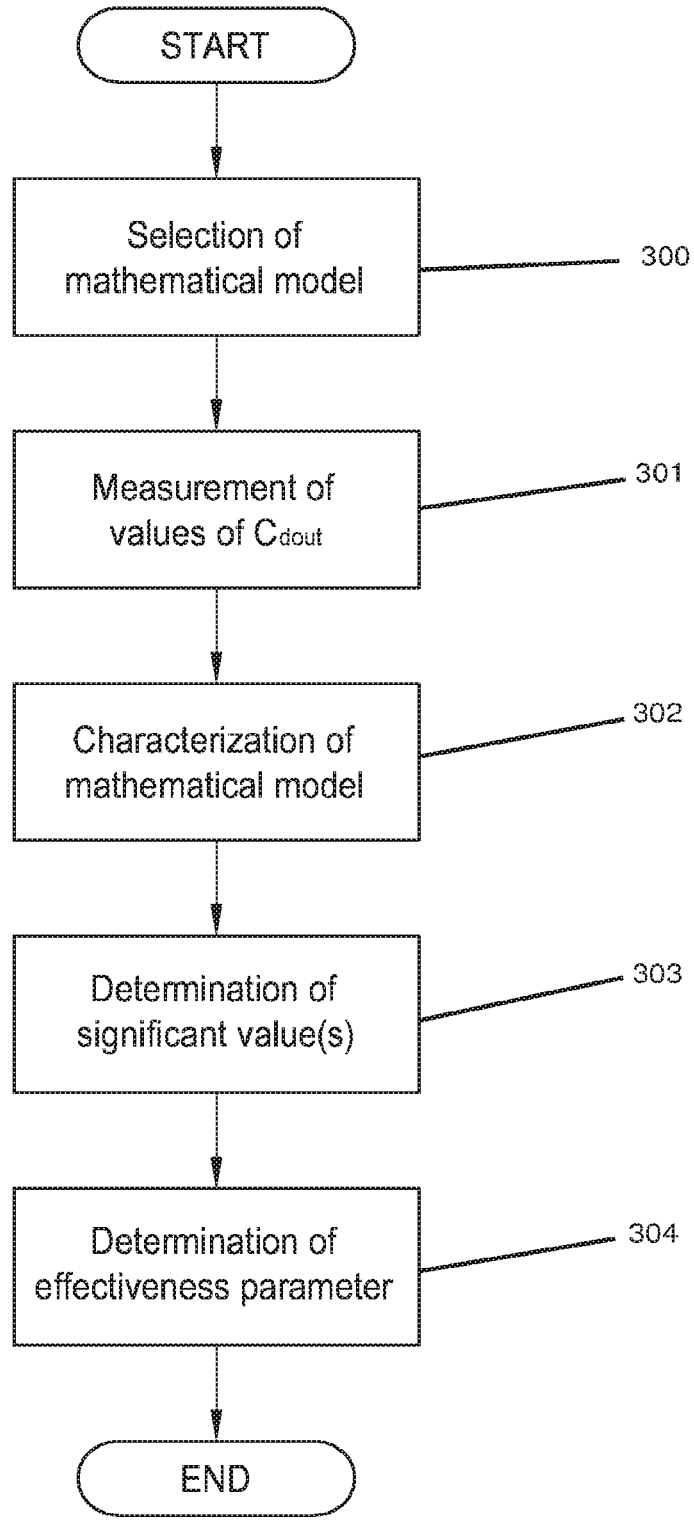
FIG. 11 is a schematic flowchart of a method according to one aspect of the invention.

Aspects of the invention are also disclosed in FIG. 11, which shows a flowchart exemplifying a method for determining an effectiveness parameter. The method may be executed by the control unit 10 of any one of the apparatuses disclosed herein above or claimed in the appended claims.

The method comprises the following steps.

step 300: selection of the mathematical model;

step 301: measurement of values of conductivity, or concentration, $Cd_{out}$ in the spent dialysate corresponding to a variation respectively in the conductivity, or in the concentration of at least one substance, $Cd_{in}$ made on the fresh dialysis liquid flowing upstream the blood treatment unit (step 301); the measures are taken during the reference time $\Delta T_R$ which is sensibly shorter than the duration of the downstream variation, as already explained herein above;

step 302: characterization of mathematical model using the measured value(s) of $Cd_{out}$ taken during the reference time $\Delta T_R$ and identification of a single mathematical model;

step 303: determination, using the mathematical model, of significant value(s) necessary for the calculation of the effectiveness parameter; the significant values may be one or more calculated conductivity or concentration values of the downstream variation at instants following the reference period (such as $Cd_{out2}$ or $Cd_{out2}$ and $Cd_{out3}$)

step 304: determination of effectiveness parameter using the calculated significant value or values.

The calculation of the effectiveness parameter may be made using any one of the formulas described above.

EXAMPLE

Here below an example is described, with reference to FIGS. 12-15, showing use of a one-zero and three-pole mathematical model to mathematically calculate the entire downstream variation; it is relevant noticing that to characterize the model, only measured values relative to a reference portion of the downstream variation having relatively short duration compared to the duration of the entire downstream variation are used. The Example provided adopts an exemplifying mathematical model and makes reference to a step perturbation imposed in the liquid flowing upstream the blood treatment unit. Of course other mathematical models may be adopted and the upstream perturbation may be different from a step-shaped perturbation. Furthermore, the example makes reference to conductivity variations and corresponding measures: of course the same procedure may be adopted using variations, and corresponding measures, in the concentration of at least one substance in the dialysis liquid.

Figure 12:
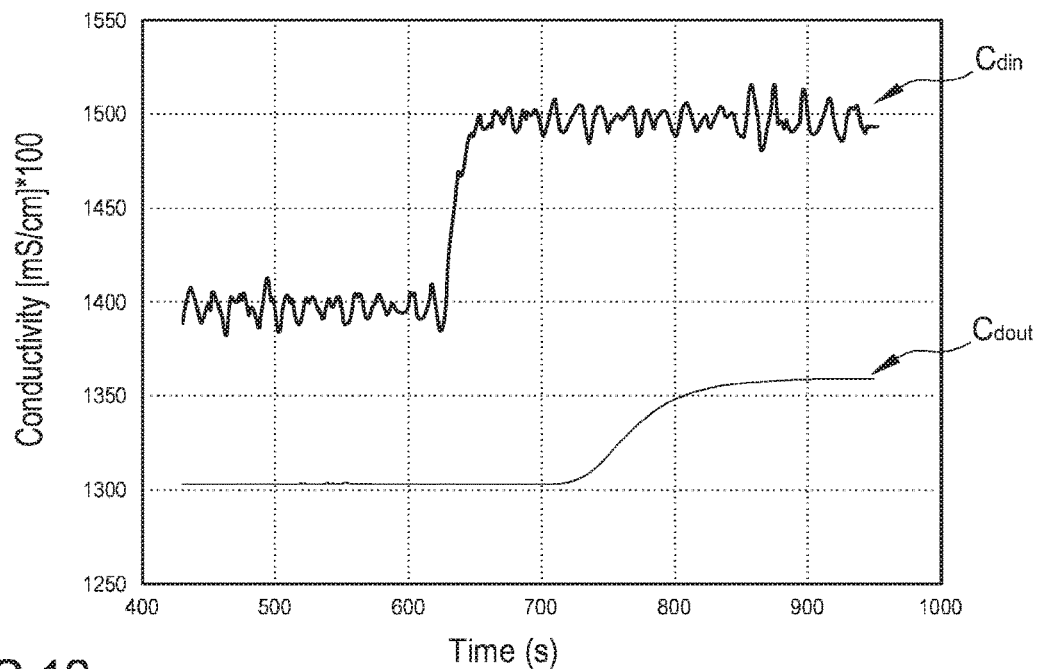
FIG. 12 shows a conductivity (mS·100/cm) vs. time (seconds) diagram showing the real measured conductivity profile in the fresh and in the spent dialysate line in the case of a step conductivity variation in the fresh dialysate of 1 mS/cm.
Figure 13:
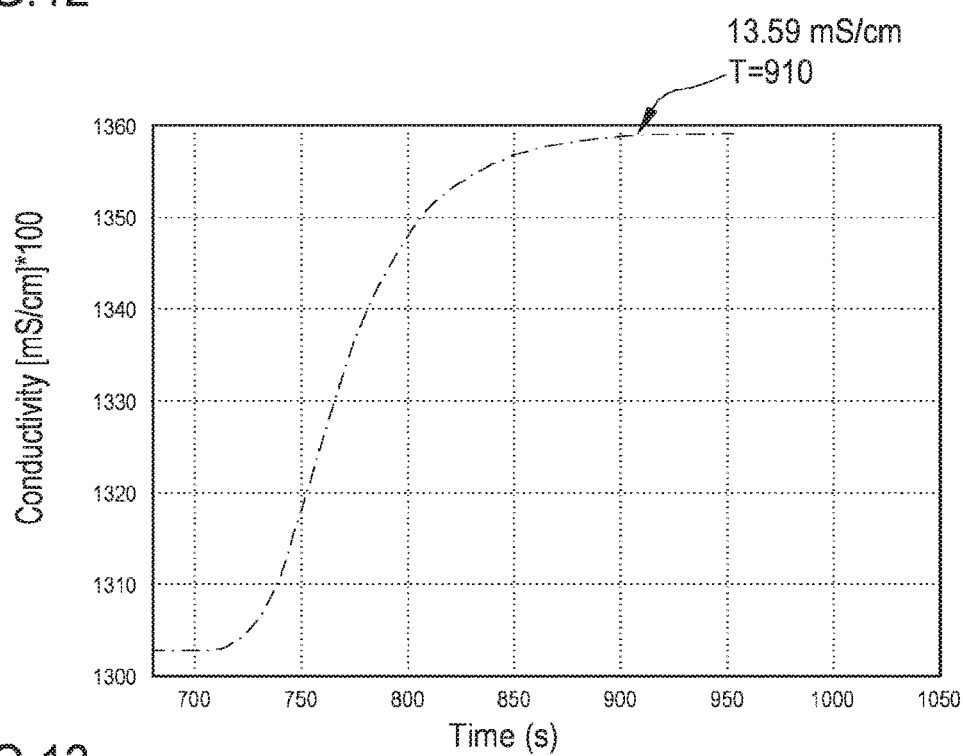
FIG. 13 is an enlarged view of the measured outlet conductivity profile of FIG. 12.
Figure 14:
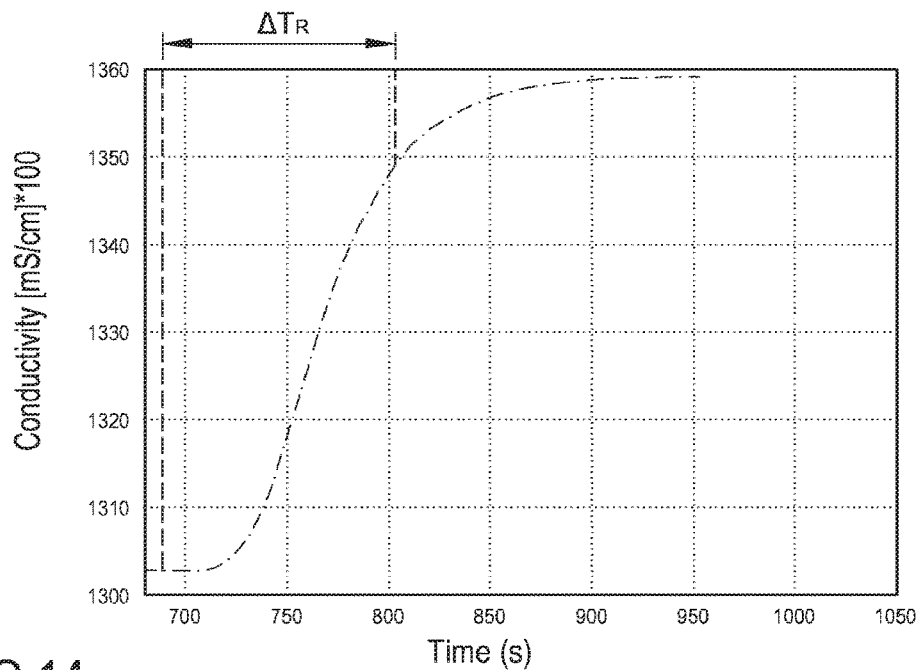
FIG. 14 is an enlarged view of the measured outlet conductivity profile of FIG. 12 where the reference time $\Delta_{TR}$ is identified.

Referring now to the diagram of FIG. 12, two curves are represented: a first curve represents the inlet conductivity $Cd_{in}$ and shows a step-shaped conductivity variation (1 mS/cm) that has been imposed to the conductivity of the dialysis liquid flowing upstream the blood treatment unit, while a second curve (below the first curve) represents the downstream conductivity $Cd_{out}$ and shows the corresponding variation in the conductivity of the spent dialysis liquid as a consequence of the step-shaped perturbation on the upstream conductivity $Cd_{in}$. FIG. 13 is an enlarged view of FIG. 12 and focuses on the outlet conductivity: notice that the curve in FIG. 13 is obtained measuring the outlet conductivity values from time 700 s to time 950 s (i.e. 250 seconds). FIG. 13 shows the value of the outlet conductivity $Cd_{out2}$ at time 910 which is regarded as the significant value of interest, necessary for the calculation of e.g. dialysance when using formula:

$$D_k = (Qd + WLR) \cdot [1 - (Cd_{out2} - Cd_{out1})]/(Cd_{in2} - Cd_{in1})$$

According to one aspect of the invention, instead of measuring the conductivity values until time 950 s, measures are taken only during reference portion $\Delta T_R$ (please refer to FIG. 14) i.e. for the 100 seconds only.

Then, using the following a one-zero and three-pole model:

$$H(z) = \frac{a_0}{a - b_1 z^{-1} - b_2 z^{-2} - b_3 z^{-3}}$$

The following parameters are estimated using the measured values of $Cd_{out}$ during reference portion $\Delta T_R$:
a0=0.004209932871
b1=−2.905495405197
b2=2.815777778625
b3=−0.910210132599
giving $$H(z) = \frac{0.004209932871}{1 - 2.905495405197 z^{-1} + 12.815777778625 z^{-2} + 0.910210132599 z^{-3}}$$

Figure 15:
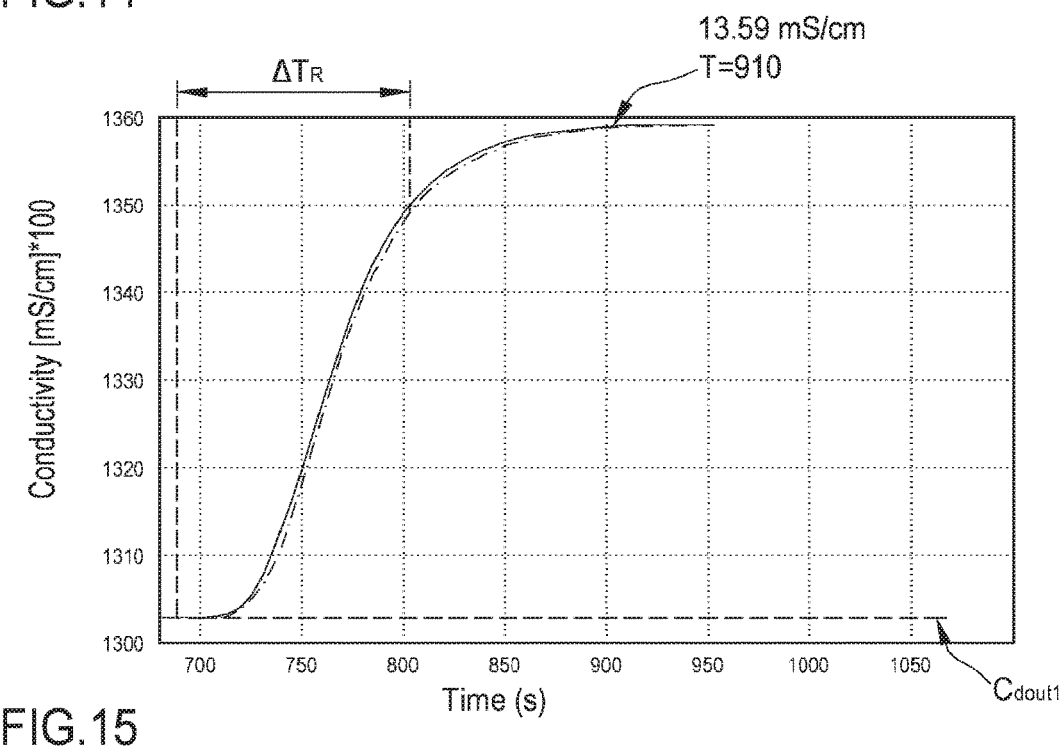
FIG. 15 is an enlarged view of the measured outlet conductivity profile of FIG. 12 (dotted line) and of the calculated curve representing the outlet conductivity as determined using a mathematical model according to aspects of the invention.

By feeding an idealized unit step (i.e. a calculated step) of appropriate length (e.g. 200 to 300 s) to this model and by suitably adding the baseline value $Cd_{out1}$ to the model output, we get a signal as shown in FIG. 15 (continuous line represents model output, while dotted line schematically represents measured $Cd_{out}$), which closely approximates the behavior of the system in a time interval following the reference portion.

The following table shows the measured versus computed values of $Cd_{out}$ in the neighborhood of time n=910 where the good match between measured and computed values can be seen.

| Time | $Cd_{out}$ model (mS · 100/cm) | $Cd_{out}$ measured (mS · 100. cm) |
|---|---|---|
| 905 | 1358.567173 | 1359 |
| 906 | 1358.586262 | 1359 |
| 907 | 1358.604656 | 1359 |
| 908 | 1358.622398 | 1359 |
| 909 | 1358.639698 | 1359 |
| 910 | 1358.656872 | 1359 |
| 911 | 1358.674126 | 1359 |
| 912 | 1358.691517 | 1359 |
| 913 | 1358.709053 | 1359 |
| 914 | 1358.726700 | 1359 |
| 915 | 1358.744549 | 1359 |

The calculated significant value $Cd_{out2}$ at time 910 is 13.59 mS/cm is very close to the corresponding measured value (13,58656872 mS/cm). Thus, the dialysance calculation using the above formula and relying on the calculated value $Cd_{out2}$ of 13.59 mS/cm will provide exactly the same result as when using a measured valued for $Cd_{out2}$, while requiring actual measurements only during $\Delta T_R$.

Control Unit 10

As already indicated the apparatus according to the invention makes use of at least one control unit 10. This control unit 10 may comprise a digital processor (CPU) with memory (or memories), an analogical type circuit, or a combination of one or more digital processing units with one or more analogical processing circuits. In the present description and in the claims it is indicated that the control unit 10 is "configured" or "programmed" to execute certain steps: this may be achieved in practice by any means which allow configuring or programming the control unit 10. For instance, in case of a control unit 10 comprising one or more CPUs, one or more programs are stored in an appropriate memory: the program or programs containing instructions which, when executed by the control unit 10, cause the control unit 10 to execute the steps described and/or claimed in connection with the control unit 10. Alternatively, if the control unit 10 is of an analogical type, then the circuitry of the control unit 10 is designed to include circuitry configured, in use, to process electric signals such as to execute the control unit 10 steps herein disclosed.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and the scope of the appended claims.

The invention claimed is:

1. An apparatus for extracorporeal blood treatment comprising:
    a blood treatment unit having a primary chamber and a secondary chamber separated by a semi-permeable membrane;
    a preparation line in fluid communication with an inlet of the secondary chamber of the blood treatment unit and configured to convey fresh treatment liquid to the secondary chamber, the fresh treatment liquid presenting a characteristic ($Cd_{in}$) which is one selected from the group of:
        conductivity in the fresh treatment liquid, and
        concentration of at least one substance in the fresh treatment liquid;
    a spent dialysate line in fluid communication with an outlet of said secondary chamber and configured to remove spent liquid from the secondary chamber, the spent liquid presenting a characteristic ($Cd_{out}$) which is one selected from the group of:
conductivity in the spent liquid, and
concentration of at least one substance in the spent liquid; and
a control unit configured to command execution of a task for determination of a parameter indicative of the effectiveness of the extracorporeal blood treatment, said task comprising:
receiving at least one prescription baseline ($Cd_{set}$) for the characteristic ($Cd_{in}$) in the fresh treatment liquid;
causing the fresh treatment liquid to flow in the preparation line to the secondary chamber with the characteristic being at said prescription baseline ($Cd_{set}$);
causing the spent liquid to flow out of the secondary chamber into the spent dialysate line;
causing an upstream variation of the characteristic ($Cd_{in}$) in the fresh treatment liquid with respect to said prescription baseline ($Cd_{set}$) thereby causing a corresponding and timely delayed downstream variation of the same characteristic ($Cd_{out}$) in the spent liquid flowing in the spent dialysate line;
measuring a plurality of values taken by a reference portion of said downstream variation of the characteristic ($Cd_{out}$) in the spent liquid, said reference portion having duration shorter than the entire duration of the downstream variation;
determining a downstream curve ($Cd_{out(t)}$) representative of the values taken by the characteristic ($Cd_{out}$) in the spent liquid for the entire duration of the downstream variation;
computing one or more significant value of said downstream variation of the characteristic ($Cd_{out}$), said one or more significant value of the downstream variation relating to a time subsequent to the duration of the reference portion; and
computing at least one value of a parameter indicative of the effectiveness of the extracorporeal blood treatment by using said one or more significant value of said downstream variation of the characteristic ($Cd_{out}$) in the spent liquid.

2. The apparatus of claim 1, wherein the step of computing at least one value of the parameter indicative of the effectiveness of the extracorporeal blood treatment comprises:
computing, by using a characteristic mathematical model, said one or more significant value of said downstream variation of the characteristic ($Cd_{out}$); and
computing at least one value of the parameter indicative of the effectiveness of the extracorporeal blood treatment from said computed one or more significant value and from one or more value taken by the characteristic ($Cd_{in}$) in the fresh treatment liquid.

3. The apparatus of claim 2, wherein said reference portion has a duration which is less than 50% compared to the duration of an entire downstream perturbation.

4. The apparatus of claim 1, wherein the control unit is configured to set, or to allow setting of, the duration of the said reference portion.

5. The apparatus of claim 1, wherein said task further comprises:
receiving at least one parametric mathematical model which puts into relation the characteristic ($Cd_{in}$) in the fresh treatment liquid with the characteristic ($Cd_{out}$) in the spent liquid, said parametric mathematical model presenting a prefixed number of free parameters;
estimating said free parameters of the at least one parametric mathematical model by means of said reference portion measured values and identifying one single characteristic mathematical model which puts into relation the characteristic ($Cd_{in}$) in the fresh treatment liquid with the characteristic ($Cd_{out}$) in the spent liquid;
computing at least one value of the parameter indicative of the effectiveness of the extracorporeal blood treatment by using said characteristic mathematical model and one or more value taken by the characteristic ($Cd_{in}$) in the fresh treatment liquid.

6. The apparatus of claim 1, wherein computing one or more significant value of said delayed variation of the characteristic ($Cd_{out}$) comprises determining the value ($Cd_{out}(n)$) of the characteristic ($Cd_{out}$) in the spent liquid at time instant (n) by using as an input to a characteristic mathematical model:
the values of the characteristic ($Cd_{in}$) in the fresh treatment liquid at a plurality of time instants (n−1, n−2, n−3) preceding in time the time instant (n); or
a mathematically calculated version of the characteristic ($Cd_{in}$) in the fresh treatment liquid.

7. The apparatus of claim 6, wherein computing one or more significant value of said delayed variation of the characteristic ($Cd_{out}$) comprises determining the value ($Cd_{out}(n)$) of the characteristic ($Cd_{out}$) in the spent liquid at time instant (n) subsequent to said reference portion with the following recursive equation, which represents the parametric mathematical model in the time domain:

$$Cd_{out}(n)=a_0 \cdot Cd_{in}(n)+b_1 \cdot Cd_{out}(n-1)+b_2 \cdot Cd_{out}(n-2)+ \ldots b_m \cdot Cd_{out}(n-m),$$

wherein:
$Cd_{out}(n)$ is the calculated value of the outlet characteristic at time instant (n),
$Cd_{in}(n)$ is the known value of the inlet characteristic at time instant (n),
$Cd_{out}(n-1)$, $Cd_{out}(n-2)$, ..., $Cd_{out}(n-m)$ are values of the outlet characteristic at preceding time instants (n−1, n−2, ... n−m) prior to time instant (n) and recursively computed by means of the mathematical model, and
$a_0$, $b_1$, $b_2$, ..., $b_m$ are constant parameters of the mathematical model, as estimated by using said measured values of the reference portion of the downstream variation.

8. The apparatus of claim 7, wherein the mathematical model is a time invariant linear (LTI) model, and wherein, in the frequency domain and using the z-Transform, the mathematical model is described by a transfer function H(z) having at least one zero and at least one pole.

9. The apparatus of claim 8, wherein the transfer function H(z) comprises from 3 to 5 poles and is described by one of the following:

$$H(z)=Cd_{out}(z)/Cd_{in}(z)=a_0/(1-b_1 \cdot z^{-1}-b_2 \cdot z^{-2}-b_3 \cdot z^{-3}-b_4 \cdot z^{-4}-b_5 \cdot z^{-5}),$$

$$H(z)=Cd_{out}(z)/Cd_{in}(z)=a_0/(1-b_1 \cdot z^{-1}-b_2 \cdot z^{-2}-b_3 \cdot z^{-3}-b_4 \cdot z^{-4}),$$

$$H(z)=Cd_{out}(z)/Cd_{in}(z)=a_0/(1-b_1 \cdot z^{-1}-b_2 \cdot z^{-2}-b_3 \cdot z^{-3}), \text{ or}$$

$$H(z)=Cd_{out}(z)/Cd_{in}(z)=a_0/(1-b_1 \cdot z^{-1}-b_2 \cdot z^{-2}),$$

wherein
$a_0$, $b_1$, $b_2$, $b_3$, $b_4$, $b_5$ are constant parameters of the mathematical model, as estimated by using said measured values of the reference portion of the downstream variation.

10. The apparatus of claim 1, comprising:

a memory connected to the control unit and storing one or more change setting procedure, each change setting procedure when executed by the control unit configuring the control unit to vary the value of the characteristic of the fresh dialysis liquid from said set value to a new set value, said control unit being further configured to:
prevent execution of the change setting procedure only until end of a measurement instant ($T_{END\_MEAS}$) at which the measurement of said plurality of values of the reference portion of said downstream variation in the characteristic ($Cd_{out}$) in the spent liquid has been completed, and allow execution of the change setting procedure immediately after the end of measurement instant ($T_{END\_MEAS}$).

11. The apparatus of claim 10, wherein the control unit is further configured to:

receive a total treatment time (T), consecutively repeat at time intervals said task for the determination of the parameter during the treatment time (T) such that a plurality of values indicative of said parameter are correspondingly determined, and allow execution of one or more change setting procedure between two consecutive tasks.

12. The apparatus of claim 1, wherein:

varying the value of the characteristic ($Cd_{in}$) in the fresh treatment liquid comprises imposing a change from a first inlet value ($Cd_{in1}$) to a second inlet value ($Cd_{in2}$), which is kept constant for a prefixed time interval, thereby causing a corresponding change of the characteristic ($Cd_{out}$) in the spent liquid from a respective first outlet value ($Cd_{out1}$) to a respective second outlet value ($Cd_{out2}$) defining said timely delayed downstream variation of the characteristic ($Cd_{out}$), the reference portion of said downstream variation begins after the characteristic in the spent liquid changes from said first outlet value ($Cd_{out1}$) and lasts a period during which the characteristic either continuously increases or decreases without reaching the second outlet value ($Cd_{out2}$), and the control unit is further configured to:
calculate the second outlet value ($Cd_{out2}$) of the characteristic ($Cd_{out}$) using the determined downstream curve ($Cd_{out(t)}$) representative of the values taken by the characteristic ($Cd_{out}$) in the spent liquid for the entire duration of the downstream variation, and use the calculated second outlet value ($Cd_{out2}$) as a significant value for the computation of at least one value of a parameter indicative of the effectiveness of the extracorporeal blood treatment.

13. The apparatus of claim 12, wherein:

calculating the second outlet value ($Cd_{out2}$) of the characteristic ($Cd_{out}$) includes using a characteristic mathematical model having as input the characteristic ($Cd_{in}$) in the fresh treatment liquid, or a mathematically calculated version of the characteristic ($Cd_{in}$) in the fresh treatment liquid.

14. The apparatus of claim 1, wherein:

varying the value of the characteristic ($Cd_{in}$) in the fresh treatment liquid comprises changing from a first inlet value ($Cd_{in1}$) to a second inlet value ($Cd_{in2}$), and then changing to a third inlet value ($Cd_{out3}$) thereby causing a corresponding time delayed downstream variation of the characteristic ($Cd_{out}$) in the spent liquid comprising a change from a respective first outlet value ($Cd_{out1}$) to a respective second outlet value ($Cd_{out2}$) and then to a third out value ($Cd_{out3}$);

the reference portion of the downstream variation begins after the characteristic in the spent liquid changes from said first outlet value ($Cd_{out1}$) and lasts a period shorter than a fraction of the duration of said downstream variation; and calculating as a significant value at least the third outlet value ($Cd_{out3}$) or both the second and the third outlet values ($Cd_{out2}$, $Cd_{out3}$) of the characteristic ($Cd_{out}$) using the determined downstream curve ($Cd_{out(t)}$) representative of the values taken by the characteristic ($Cd_{out}$) in the spent liquid for the entire duration of the downstream variation.

15. The apparatus of claim 14, wherein:

calculating as a significant value at least the third outlet value ($Cd_{out3}$) or both the second and the third outlet values ($Cd_{out2}$, $Cd_{out3}$) of the characteristic ($Cd_{out}$) includes using a characteristic mathematical model having as input the characteristic ($Cd_{in}$) in the fresh treatment liquid, or a mathematically calculated version of the characteristic ($Cd_{in}$) in the fresh treatment liquid.

16. The apparatus of claim 1, wherein:

varying the value of the characteristic ($Cd_{in}$) in the fresh treatment liquid comprises imposing an upstream perturbation in the characteristic of the fresh treatment liquid thereby causing a corresponding downstream perturbation of the characteristic ($Cd_{out}$) in the spent liquid, the reference portion of said downstream perturbation begins after the characteristic in the spent liquid changes from said first outlet value ($Cd_{out1}$) and lasts a prefixed period shorter than 60% of the duration of the downstream perturbation, and the control unit is further configured to:
extrapolate a plurality of significant values of the characteristic ($Cd_{out}$), describing a remaining portion of the downstream perturbation consecutive to said reference portion, obtain a calculated downstream perturbation from said extrapolated significant values, and compute at least one value of a parameter indicative of the effectiveness of the extracorporeal blood treatment by comparing the calculated downstream perturbation and the upstream perturbation.

17. The apparatus of claim 1, wherein the reference portion of said downstream variation lasts a period during which the characteristic either continuously increases or decreases without reaching 80% of the second outlet value ($Cd_{out2}$).

18. The apparatus of claim 1, wherein said parameter comprises one selected from the group of:

an effective dialysance for one or more substances of the treatment unit (D), an effective clearance for one or more substances of the treatment unit (K), a concentration of a substance in blood ($Cb_{in}$) upstream the blood treatment unit, or a dialysis dose at time (t) after start of the treatment (K·t/V).

19. The apparatus of claim 18, wherein the parameter comprises the effective dialysance (D) and wherein each computed value ($D_k$) of said parameter at each respective variation is obtained using the formula $$D_k = (Qd + WLR) \cdot [1 - (Cd_{out2} - Cd_{out1})]/(Cd_{in2} - Cd_{in1})$$

wherein $Cd_{out1}$ is the first outlet value taken by the characteristic in the spent dialysate line downstream of the secondary chamber in response to the change of characteristic ($Cd_{in}$) in the preparation line to said first inlet value $Cd_{in1}$, $Cd_{out2}$ is the second value taken by the characteristic in the spent dialysate line downstream of the secondary chamber in response to the change of the characteristic ($Cd_{in}$) in the preparation line at said second inlet value ($Cd_{in2}$), $Cd_{in1}$, $Cd_{in2}$ are first and second inlet values taken by the characteristic (Cd) in the preparation line upstream of the secondary chamber, Qd is the fresh treatment liquid flow rate in the preparation line, and WLR is the weight loss rate of a patient under treatment; or the formula $$D_K = (Qd+WLR)[1-(2 \times Cd_{out1} - Cd_{out2} - Cd_{out3})/(2 \times Cd_{in1} - Cd_{in2} - Cd_{in3})]$$

wherein $Cd_{out1}$ is the first outlet value taken by the characteristic in the spent dialysate line downstream of the secondary chamber in response to the change of characteristic ($Cd_{in}$) in the preparation line to said first inlet value ($Cd_{in1}$), $Cd_{out2}$ is the calculated second value which is representative of the value taken by the characteristic in the spent dialysate line downstream of the secondary chamber in response to the change of characteristic ($Cd_{in}$) in the preparation line from said first inlet value ($Cd_{in1}$) to said second inlet value ($Cd_{in2}$), $Cd_{out3}$ is the calculated third value which is representative of the value taken by the characteristic in the spent dialysate line downstream of the secondary chamber in response to the change of characteristic ($Cd_{in}$) in the preparation line from said second inlet value ($Cd_{in2}$) to said third inlet value ($Cd_{in3}$), $Cd_{in1}$, $Cd_{in2}$, $Cd_{in3}$ are first, second and third inlet values taken by the characteristic (Cd) in the preparation line upstream of the secondary chamber, Qd is the fresh treatment liquid flow rate in the preparation line, and WLR is the weight loss rate of a patient under treatment.

20. The apparatus of claim 1, wherein the control unit is configured to:

determine a downstream curve ($Cd_{out(t)}$) representative of the values taken by the characteristic ($Cd_{out}$) in the spent liquid, determine an angular deviation of a downstream baseline of the downstream curve ($Cd_{out(t)}$) with respect to the prescription baseline ($Cd_{set}$), and compensate for said angular deviation by angularly rotating the downstream curve to obtain a corrected downstream curve ($Cd_{out-correct(t)}$).

21. The apparatus of claim 20, wherein the step of determining a downstream curve ($Cd_{out(t)}$) representative of the values taken by the characteristic ($Cd_{out}$) in the spent liquid comprises:

using measured values across a time interval covering at least the entire downstream variation; or measuring values of the characteristic ($Cd_{out}$) in the spent liquid until the end of said reference portion, estimating the free parameters of a parametric mathematical model to identify a characteristic mathematical model, and using said identified characteristic mathematical model to calculate the downstream curve ($Cd_{out(t)}$).

22. The apparatus of claim 1, wherein the control unit is configured to:

determine a downstream curve ($Cd_{out(t)}$) representative of the values taken by the characteristic ($Cd_{out}$) in the spent liquid, analyze a frequency spectrum of the downstream curve ($Cd_{out(t)}$), and filter out harmonics of said frequency spectrum of the downstream curve ($Cd_{out(t)}$) lying at frequencies higher than a prefixed threshold to eliminate noise and undesired perturbations possibly present in the downstream curve and obtain a corrected downstream curve ($Cd_{out-correct(t)}$).

23. The apparatus of claim 22, wherein the step of determining a downstream curve ($Cd_{out(t)}$) representative of the values taken by the characteristic ($Cd_{out}$) in the spent liquid comprises:

using measured values across a time interval covering at least the entire downstream variation, or measuring values of the characteristic ($Cd_{out}$) in the spent liquid until the end of said reference portion, estimating the free parameters of a parametric mathematical model to identify a characteristic mathematical model, and using said identified characteristic mathematical model to calculate the downstream curve ($Cd_{out(t)}$).

24. The apparatus of claim 1, wherein the control unit is further configured to:

store a plurality of mathematical models each of which puts into relation the characteristic ($Cd_{in}$) in the fresh treatment liquid with the characteristic ($Cd_{out}$) in the spent liquid; and select one mathematical model to be used for computing the at least one significant value of said downstream variation based at least on one selected from the group of: (i) the shape of said upstream variation; and (ii) the type of blood treatment unit used by the apparatus.

* * * * *